United States Patent [19]

Igo et al.

[11] Patent Number: 5,634,895
[45] Date of Patent: Jun. 3, 1997

[54] APPARATUS AND METHOD FOR TRANSPERICARDIAL DELIVERY OF FLUID

[75] Inventors: Stephen R. Igo, Clear Lake Shores; James W. Meador, Houston, both of Tex.

[73] Assignee: Cormedics Corp., Clear Lake Shores, Tex.

[21] Appl. No.: 486,104

[22] Filed: Jun. 7, 1995

Related U.S. Application Data

[62] Division of Ser. No. 264,458, Jun. 23, 1994.

[51] Int. Cl.⁶ .................................................. A61B 17/36
[52] U.S. Cl. ................... 604/21; 604/20; 604/96; 604/49; 604/53
[58] Field of Search ............... 604/96, 101, 19, 604/20, 21, 51, 93, 390.1, 391.1; 600/191–194

[56] References Cited

U.S. PATENT DOCUMENTS

| | | | |
|---|---|---|---|
| 4,411,648 | 10/1983 | Davis | 604/21 |
| 4,423,725 | 1/1984 | Baran | 604/101 |
| 4,751,924 | 6/1988 | Hammerscmidt et al. | 604/101 |
| 4,809,707 | 3/1989 | Kraft et al. | 128/736 |
| 5,163,905 | 11/1992 | Don Michael | 604/101 |
| 5,176,638 | 1/1993 | Don Michael | 604/101 |
| 5,178,608 | 1/1993 | Winters | 604/101 |
| 5,222,936 | 6/1993 | Stephen | 604/21 |
| 5,236,413 | 8/1993 | Feiring | 604/21 |
| 5,279,546 | 1/1994 | Mische et al. | 604/101 |
| 5,282,785 | 2/1994 | Shapland et al. | 604/21 |
| 5,286,254 | 2/1994 | Shapland et al. | 604/21 |
| 5,318,531 | 6/1994 | Leone | 604/101 |
| 5,380,319 | 1/1995 | Saito | 604/101 |
| 5,397,307 | 3/1995 | Goodin | 604/101 |
| 5,421,818 | 6/1995 | Arenberg | 604/21 |

*Primary Examiner*—Corrine M. McDermott
*Assistant Examiner*—Chalin Smith
*Attorney, Agent, or Firm*—Tim L. Burgess

[57] ABSTRACT

Method and apparatus for treating blood vessels in a mammal, particularly humans, especially coronary blood vessels, for vascular thrombosis and angioplasty restenosis, thereby to decrease incidence of vessel rethrombosis, unstable angina and myocardial infarction, by administering a conager of an endothelium-derived bioactive agent, especially a nitrovasodilator, including one or more of nitric oxide or a nitric oxide donor agent, such as sodium nitroprusside and nitroglycerin, to an extravascular treatment site at a therapeutically effective dosage rate.

23 Claims, 15 Drawing Sheets

APPARATUS AND METHOD FOR TRANSPERICARDIAL DELIVERY OF FLUID

This application is a division of U.S. patent application Ser. No. 08/264,458, filed on Jun. 23, 1994.

BACKGROUND OF THE INVENTION

This invention relates to methods and devices for the site-specific delivery of bioactive agents in mammals, especially for cardiac and peripheral vascular applications, and more particularly, as respects application for coronary thrombolysis and revascularization procedures, to methods and devices for prevention of coronary vasoconstriction, vascular thrombosis and restenosis during and after percutaneous transluminal coronary angioplasty and for prevention of coronary artery bypass graft thrombosis and occlusion.

1. Pathophysiological Background

A. Vascular Endothelium Function

Normal blood vessels are lined with a layer of endothelial cells. The endothelium releases local factors (endothelium-derived relaxing factor [nitric oxide] and prostaglandin $I_2$ [$PGI_2$, or prostacyclin]) into the vessel wall (intramural release) and into the blood stream (intraluminal release). These factors maintain vascular tone (vessel relaxation), inhibit clot formation on the vessel inner surface (platelet adhesion and aggregation), inhibit monocyte adherence and chemotaxis, and inhibit smooth muscle cell migration and proliferation. Normal endothelium releases both prostacyclin and nitric oxide in response to platelet aggregation. Nitric oxide release inhibits platelet adhesion, prevents further aggregation, and promotes platelet disaggregation. Prostacyclin release, promoted by platelet-derived thromboxane $A_2$, acts synergistically with nitric oxide to prevent platelet-mediated vasoconstriction. As a result of this process, vasodilation and thrombolysis occurs, and blood flow is maintained. If the endothelium is dysfunctional or damaged, however, nitric oxide and prostacyclin release is impaired. Platelet aggregation and adhesion can occur unopposed, with platelet-derived products acting directly on the smooth muscle cells to cause vasoconstriction. The net result is a blood vessel which is highly susceptible to thrombosis and vasospasm. See, "Nitric oxide release accounts for the biological activity of endothelium-derived relaxing factor", Palmer R., et al., NATURE, 327:524, 1987; "Control of coronary vascular tone by nitric oxide", Kelm M., et al., CIRC. RES., 66:1561, 1990; "Regulatory functions of the vascular endothelium", Vane J., et al., N. ENCL. J. MED., 323:27, 1990; "Endothelial modulation of vascular tone: Relevance to coronary angioplasty and restenosis", Harrison D., J. AMER. COL. CARDIOL., 17:71B, 1991; "The antiaggregating properties of vascular endothelium: Interactions between prostacyclin and nitric oxide", Radomski M., et al., BRIT. J. PHARMACOL., 92:639, 1987; "EDRF increases cyclic GMP in platelets during passage through the coronary vascular bed", Pohl U., et al., CIRC. RES., 65:1798, 1989; "Human endothelial cells inhibit platelet aggregation by separately stimulating platelet cAMP and cGMP", Alheid U., et al., EUROP. I. PHARMACOL., 164:103, 1989; "Nitric oxide: An endogenous modulator of leukocyte adhesion", Kubes P., et al., PROC. NATL. ACAD. SCI., 88:4651, 1991; "Nitric oxide and prostacyclin: Divergence of inhibitory effects on monocyte chemotaxis and adhesion to endothelium in vitro", Bath P., et al., ARTERIOSCLER. THROMB., 11:254, 1991; "Nitric oxide generating vasodilators and 8-Br-cGMP inhibit mitogenesis and proliferation of cultured rat vascular smooth muscle cells", Garg U., et al., J. CLIN. INVEST., 83:1774, 1989; "Role of blood platelets and prostaglandins in coronary artery disease", Mehta J., et al., AMER. J. CARDIOL., 48:366, 1981; and "Prostaglandins and cardiovascular disease: A review", Jacobsen D., SURGERY, 93:564, 1983.

B. Vascular Stenosis

Atherosclerosis can form within a blood vessel over a period of years from a variety of causes. The resulting lesion, or plaque, may progressively occlude the vessel and impede blood flow to vital organs. The stenotic lesions when covered by endothelium are termed stable. See, "Cellular proliferation in atherosclerosis and hypertension", Schwartz S., et al., PROG. CARDIOVASC. DIS., 26:355, 1984; and "The pathogenesis of atherosclerosis: An update", Ross R., N. ENGL. J. MED., 314:488, 1986.

Unstable stenotic lesions are associated with endothelial cell injury at the sites of coronary stenosis. Injury to the endothelium stops the local release of the endothelium-derived factors. Severe injury to the vessel wall exposes the underlying collagen layer, which immediately activates platelet adhesion and aggregation (clumping) and stimulates vasoconstriction (spasm). The platelet blood clotting cascade is triggered, thrombin and fibrin quickly form at the site(s) of vascular injury, and a thrombus begins forming. The aggregating platelets release local growth factor (platelet-derived growth factor or PDGF) which activates smooth muscle cells within the vessel wall. Over a period of days-to-weeks, smooth muscle cells migrate into the thrombus and proliferate, and the thrombus becomes organized. See, "The restenosis paradigm revisited: An alternative proposal for cellular mechanisms", Schwartz R., et al., J. AMER. COL. CARDIOL., 20:1284, 1992; "The pathogenesis of coronary artery disease and the acute coronary syndromes: Parts I and II", Fuster V., et al., N. ENCL. J. MED., 326:242 and 310, 1992; "Migration of smooth muscle and endothelial cells", Casscells W., CIRC., 86:723, 1992; "The role of platelets, thrombin and hyperplasia in restenosis after coronary angioplasty", Ip J., et al., J. AMER. COL. CARDIOL., 17:77B, 1991; "Syndromes of accelerated atherosclerosis: Role of vascular injury and smooth muscle cell proliferation", Ip J., et al., J. AMER. COL. CARDIOL., 15:1667, 1990; "Time course of smooth muscle cell proliferation in the intima and media of arteries following experimental angioplasty", Hanke H., et al., CIRC. RES., 67:651, 1990; "Effect of platelet factors on migration of cultured bovine aortic endothelial and smooth muscle cells", Bell L., et al., CIRC. RES., 65:1057, 1989; "Role of platelets in smooth muscle cell proliferation and migration after vascular injury in rat carotid artery", Fingerle J., et al., PROC. NATL. ACAD. SCI., 86:8412, 1989; "Restenosis after coronary angioplasty: Potential biologic determinants and role of intimal hyperplasia", Liu M., et al., CIRC., 79:1374, 1989; "Is vasospasm related to platelet deposition?", Lam J., et al., CIRC., 75:243, 1988; "Role of platelets and thrombosis in mechanisms of acute occlusion and restenosis after angioplasty", Harker L., AMER. J. CARDIOL., 60:20B, 1987; and "Restenosis after arterial angioplasty: A hemorrheologic response to injury", Chesebro J., et al., AMER. J. CARDIOL., 60:10B, 1987.

C. Coronary Artery Stenosis

The described vasoconstrictive physiologic mechanisms occur both in peripheral and in coronary arteries, but the consequences of the processes are more life threatening in the coronary arteries. Coronary arteries, the arteries of the heart, perfuse the cardiac muscle with oxygenated arterial blood. They provide essential nutrients and allow for metabolic waste and gas exchange. These arteries are subject to unremitting service demands for continuous blood flow throughout the life of the patient. A severe proximal coronary artery stenosis with endothelial injury induces cyclic coronary flow reductions ("CFR's"). These are periodic or spasmodic progressive reductions in blood flow in the injured artery. Episodes of CFR's are correlated to clinical acute ischemic heart disease syndromes, which comprise unstable angina, acute myocardial infarction and sudden death. The common pathophysiologic link is endothelial injury with vasospasm and/or thrombus formation.

Coronary artery disease is the leading cause of death in the United States today. In 1992, the clinical population of unstable angina patients in the United States numbered approximately 1,000,000. Of these patients, it is estimated that 160,000 underwent coronary thrombolysis therapy where a clot dissolving agent is injected intravenously or intracoronary to reopen the thrombosed vessel and reduce the incidence of myocardial infarction and sudden death. See, *"Mechanisms contributing to precipitation of unstable angina and acute myocardial infarction: Implications regarding therapy"*, Epstein S., et al., AMER. J. CARDIOL., 54:1245, 1984; *"Unstable angina with fatal outcome: Dynamic coronary thrombosis leading to infarction and/or sudden death"*, Falk E., CIRC., 71:699, 1985; *"Speculation regarding mechanisms responsible for acute ischemic heart disease syndromes"*, Willerson J., et al., J. AMER. COL. CARDIOL., 8:245, 1986; *"Platelets and thrombolytic therapy"*, Coller B., N. ENGL. J. MED., 322:33, 1990; and *"Frequency and severity of cyclic flow alterations and platelet aggregation predict the severity of neointimal proliferation following experimental coronary stenosis and endothelial injury"*, Willerson J., et al., PROC. NATL. ACAD. SCI., 88:10624, 1991.

2. Surgical Procedures for Coronary Artery Disease
A. Procedures

Historically, the treatment of advanced atherosclerotic coronary artery disease (i.e., beyond that amenable to therapy via medication alone) has involved cardiac surgery in the form of a coronary artery bypass graft ("CABG"). The patient is placed on cardiopulmonary bypass (heart-lung machine) and the heart muscle is temporarily stopped (cardioplegia). Repairs are then surgically affected on the heart in the form of detour conduit grafted vessels (vein or artery graft) providing blood flow around the coronary artery obstruction(s). While CABG surgery has been shown to be effective, it carries with it inherent surgical risk and requires a recuperation period of several weeks. During 1992, approximately 290,000 patients underwent CABG surgery in the United States.

A major advance in the treatment of atherosclerotic coronary artery disease occurred in the late 1970's with introduction of the less-invasive percutaneous transluminal coronary angioplasty ("PTCA") procedures. The PTCA technique involves the retrograde introduction, from an artery in the leg or arm, up to the area of coronary vascular stenosis, of a catheter with a small dilating balloon at its tip. The catheter is advanced through the arteries via direct fluoroscopic guidance and passed across the luminal narrowing of the vessel. Once in place the catheter balloon is inflated for a short period of time. This results in mechanical deformation of the lesion or vessel with a subsequent increase in the cross-sectional area. This in turn reduces obstruction and transluminal pressure gradients, and increases blood flow through the coronary artery. PTCA or angioplasty is a term that now may include other percutaneous transluminal methods of decreasing stenosis within a blood vessel, and includes not only balloon dilation, but also thermal ablation and mechanical atherectomy with shaving, extraction or ultrasonic pulverization of the lesion. During 1992 in the United States, it is estimated that some 400,000 patients underwent coronary angioplasty procedures.

B. The Problem of Vascular Restenosis

Despite the major therapeutic advances in the treatment of coronary artery disease represented by thrombolytic therapy, CABG operations and PTCA procedures, the success of these measures has been hampered by the development of vessel renarrowing or reclosure, most significantly in patients undergoing thrombolysis and angioplasty procedures. Abrupt vessel occlusion or early restenosis may develop during a period of hours to days post-procedure due to vasospasm and/or platelet thrombus formation at the site of vessel injury. The more common and major limitation, however, is a development of progressive reversion of the diseased vessel to its previous stenotic condition, negating any gains achieved from the procedure. This gradual renarrowing process is referred to as restenosis or intimal hyperplasia. Restenosis is a reparative response to endovascular injury after angioplasty and in vein grafts following vessel bypass surgery. The sequence of events is similar to that described above for unstable lesions associated with endothelial injury, progressing through the process of platelet aggregation, vasoconstriction, thrombus formation, PDGF release, smooth muscle cell proliferation, and thrombus organization.

Clinical studies indicate that thrombolytic therapy is ineffective in about 20% of the treated patients and that 20% of those patients initially responding to therapy develop vessel rethrombosis within one week. Clinical studies also indicate that significant restenosis occurs in about 40% of the PTCA patients within six months and in about 20% of the CABG patients within one year. This complication results in increased morbidity, need for repeating the procedure, and escalating medical costs. With an estimated 690,000 coronary revascularization procedures performed in the United States in 1992, these incidences mean as many as 200,000 patients may develop vessel restenosis within one year after operation. Repeat procedures could account for $2.85 billion in additional health care costs in the United States.

6. Lack of Success in Prevention of Vasular Restenosis Without Side-Effects

At present, no therapy is know that consistently prevents the major clinical problem of vascular restenosis. Intravenous medications have been tried as a means to prevent PTCA restenosis and other coronary disease syndromes. Systemically administered pravastatin (U.S. Pat. No. 4,346, 227) and lovastatin (U.S. Pat. No. 5,140,012), both HMG CoA reductase inhibitors, have been said to prevent restenosis following angioplasty. Prostaglandin $E_1$ ("PGE$_1$", a congener of endothelium-derived PGI$_2$ and prostacyclin) and a known potent vasodilator with antiplatelet, antiinflammatory and antiproliferative effects—see *"Hemodynamic effects of prostaglandin $E_1$ infusion in patients with acute myocardial infarction and left ventricular failure"*, Popat K., et al., AMER. HEART J., 103:485, 1982; *"Comparison of equimolar concentrations of iloprost, prostacyclin, and prostaglandin $E_1$ on human platelet function"*, Fisher C., et al., J. LAB. CLIN. MED., 109:184, 1987; and *"Prostaglandin $E_1$ inhibits DNA synthesis in arterial smooth muscle cells stimulated with platelet-derived growth factors"*, Nilsson J., et al., ATHEROSCLEROSIS, 53:77, 1984—has been reported to inhibit abrupt occlusion and early restenosis in patients when infused intravenously after PTCA for 12 hours at dosages of from 20 to 40 ng/kg/min following a 65 ng bolus given intracoronary before and after PTCA, *"Prostaglandin $E_1$ infusion after angiolplasty in humans inhibits abrupt occlusion and early restenosis"*, See J., et al., ADV. PROSTAGLANDIN, THROMBOXANE AND LEUKOTRIENE RES., 17:266, 1987. However, prostacyclin ($PGI_2$) did not lower the coronary restenosis rate at 5 months following PTCA, although infused intravenously for 48 hours after PTCA at dosages of 5.0 ng/kg/min following intracoronary infusion at 7.0 ng/kg/min before and after the PTCA procedure, *"Effect of short-term prostacyclin administration on restenosis after percutaneous transluminal coronary angioplasty"*, Knudtson M., et al., J. AMER. COL. CARDIOL., 15:691, 1990.

Sodium nitroprusside and other organic nitrates including nitroglycerin have long been used as vasodilator agents, and investigations, cited above, have shown that nitric oxide is the endogenous endothelium-derived nitrovasodilator: These agents also have anti-platelet effects, *"The interaction of sodium nitroprusside with human endothelial cells and platelets: Nitroprusside and prostacyclin synergistically inhibit platelet function"*, Levin R., et al., CIRC., 66:1299, 1982; *"Platelets, vasoconstriction, and nitroglycerin during arterial wall injury: A new antithrombotic role for an old drug"*, Lam J., et al., CIRC., 78:7122, 1988. In a study in stenosed and endothelium-injured canine coronary arteries, promotion of endogenous nitric oxide production by infusion of L-arginine (the precursor for nitric oxide synthesis), at a dosage of 60 mg/kg, decreased platelet aggregation and abolished CFR's, *"Endogenous nitric oxide protects against platelet aggregation and cyclic flow variations in stenosed and endothelium-injured arteries"*, Yao S., et al., CIRC., 86:1302, 1992. Intravenous nitroglycerin infusion at dosages from 10 to 15 µg/kg/min inhibited CFR's in stenosed and endothelium-injured coronary arteries of dogs. This effect was potentiated by the pretreatment with the reduced thiol, N-acetylcysteine, at a dose of 100 mg/kg for 30 minutes, *"Intravenous nitroglycerin infusion inhibits cyclic blood flow responses caused by periodic platelet thrombus formation in stenosed canine coronary arteries"*, Folts J., et al., CIRC., 83:2122, 1991. Sodium nitroprusside is also a nitric oxide donor agent, *"Metabolic activation of sodium nitroprusside to nitric oxide in vascular smooth muscle"*, Kowaluk E., et al., J. PHARMACOL. EXPER. THERAPEUTICS, 262:916, 1992.

The difficulty with systemic infusion of $PGE_1$, $PGI_2$, prostacyclin, sodium nitroprusside and the other organic nitrates is that, in dosages high enough to provide signs of beneficial cardiac effect, the potent vasodilator and anti-platelet effects of these bioactive agents also produce systemic side effects of bleeding and hypotension. No know therapy consistently prevents acute coronary thrombosis and chronic vascular restenosis while reducing the systemic side-effects of bleeding and hypotension. See, *"Prevention of restenosis after percutaneous transluminal coronary angioplasty: The search for a 'magic bullet'"*, Hermans W., et al., AMER. HEART J., 122:171, 1991; and *"Clinical trials of restenosis after coronary angioplasty"*, Popma J., et al., CIRC., 84:1426, 1991.

Recently, site-specific drug delivery to the arterial wall has become a new strategy for the treatment of vascular diseases, including vessel restenosis following PTCA. These drug delivery systems include: (1) intravascular devices for site-specific (coronary artery) drug delivery comprising double-balloon catheters, porous balloon catheters, microporous balloon catheters, channel balloon catheters, balloon over stent catheters, hydrogel coated balloon catheters, iontophoretic balloon catheters and stent devices; (2) periadventitial and epicardial drug delivery devices, requiring surgical implantation, which include drug-eluting polymer matrices and a iontophoretic patch device; and (3) intramural injection of drug-eluting microparticles. All of these methods are limited by certain problems including additional trauma to the vessel wall, rapid washout of drug, need for invasive insertion, and/or use of therapeutic agents having a single mechanism of action. See, *"Effect of controlled adventitial heparin delivery on smooth muscle proliferation following endothelial injury"*, Edelman E., et al., PROC. NATL. ACAD. SCI., 87:3773, 1990; *"Localized release of perivascular heparin inhibits intimal proliferation after endothelial injury without systemic anticoagulation"*, Okada T., et al., NEUROSURGERY, 25:892, 1989; *"Iontophoretic transmyocardial drug delivery: A novel approach to antiarrhythmic drug therapy"*, Avitall B., et al., CIRC., 85:1582, 1992; *"Direct intraarterial wall injection of microparticles via a catheter: A potential drug delivery strategy following angioplasty"*, Wilensky R., et al., AMER. HEART J., 122:1136, 1991; *"Local anticoagulation without systemic effect using a polymer heparin delivery system"*, Okada T., et al., STROKE, 19:1470, 1988.

Intrapericardial injection of drugs has been used for the treatment of malignant or loculated pericardial effusions in man. Drugs that have been injected into the pericardial space include antibiotic, antineoplastic, radioactive and fibrinolytic agents. This method of site-specific drug delivery has been shown to be effective in attaining higher, longer-lasting drug levels in the pericardial fluid with lower plasma concentrations and less systemic toxicity. It has been reported that no major complications were associated with the intrapericardial drug infusion catheter and that it was possible to repeat the procedure without difficulty. See, *"Intrapericardial instillation of platin in malignant pericardial effusion"*, Fiorentino M., et al., CANCER, 62:1904, 1988; and *"Use of streptokinase to aid drainage of postoperative pericardial effusion"*, Cross J., et al., BRIT. HEART J., 62:217, 1989.

SUMMARY OF THE INVENTION

It is an object of this invention to provide treatment of vascular thrombosis and angioplasty restenosis, particularly coronary vascular thrombosis and angioplasty restenosis, thereby to decrease incidence of vessel rethrombosis, unstable angina, myocardial infarction and sudden death.

It is an object of this invention to prevent coronary angioplasty restenosis, thereby to improve the results of the procedure, to decrease need for additional intervention and to lower health care costs.

An object of this invention is to provide nonsystemic, site-specific and time extended administration of bioactive substances at low dosages effective to achieve a desired treatment effect and localized so as not to generalize the effect systemically.

An object of this invention is to impart thrombolytic, vasodilator, antithrombotic and antiproliferative actions to injured coronary vessels with reduced systemic effects.

An object of this invention is to provide delivery systems for site-specific pharmacologic therapy effective to prevent venous bypass graft thrombosis and intimal hyperplasia in coronary artery surgery patients.

These and other objects and benefits of our invention will become apparent from the description of our invention that now follows.

We have discovered that administration of a conager of an endothelium-derived bioactive agent, more particularly a nitrovasodilator, representatively the nitric oxide donor agent sodium nitroprusside, to an extravascular treatment site, at a therapeutically effective dosage rate, is effective for abolishing CFR's while reducing or avoiding systemic effects such as supression of platelet function and bleeding. By "extravascular treatment site", we mean a site proximately adjacent the exterior of the vessel. In accordance with our invention, conagers of an endothelium-derived bioactive agent include prostacyclin, prostaglandin $E_1$, and a nitrovasodilator agent. Nitrovasodilater agents include nitric oxide and nitric oxide donor agents, including L-arginine, sodium nitroprusside and nitroglycycerine. The so administered nitrovasodilators are effective to provide one or more of the therapeutic effects of promotion of vasodilation, inhibition of vessel spasm, inhibition of platelet aggregation, inhibition of vessel thrombosis, and inhibition of platelet growth factor release, at the treatment site, without inducing systemic hypotension or anticoagulation.

The treatment site may be any blood vessel. The most acute such blood vessels are coronary blood vessels. The coronary blood vessel may be a natural artery or an artificial artery, such as a vein graft for arterial bypass.

The step of administering includes delivering the congener in a controlled manner over a sustained period of time, and comprises intrapericardially or transpericardially extravascularly delivering the congener to the coronary blood vessel. Methods of delivery comprise (i) either intrapericardially or transpericardially infusing the congener through a percutaneously inserted catheter extravascularly to the coronary blood vessel, (ii) iontophoretically delivering the congener transpericardially extravascularly to the coronary blood vessel, and (iii) inserting extravascularly to the coronary blood vessel an implant capable of extended time release of the congener. The last method of delivery includes percutaneously inserting the implant proximately adjacent, onto, or into the pericardial sac surrounding the heart, and in a particular, comprises surgically wrapping the implant around a vein graft used for an arterial bypass. The extravascular implant may be a biodegradable controlled-release polymer comprising the congener.

In accordance with our invention, an apparatus for distribution of a liquid carrying a solute (more particularly in the method of this invention, a nitrovasodilator) onto a surface of a mammal body part (more particularly in accordance with a method of this invention, the pericardium) comprises an elongated catheter body having a proximal and distal segment, the body defining first and second lumens extending therethrough. The first lumen extends into a plurality of first passages connecting the first lumen to the exterior of the distal segment, and the second lumen extends into a plurality of second passages connecting the second lumen to the exterior of the distal segment. A predominately laterally expandable bag is mounted to an outer surface of the distal segment of the body to be free over the first passages and not cover the second passages, thereby defining a bag cavity between the bag and the outer surface. The bag has a plurality of fluid outlets from the balloon cavity to an exterior portion of the bag, providing fluid communication from the first lumen to the exterior portion. A predominately vertically expandable second balloon is mounted to an outer surface of the distal segment of the body to be free over the second passages and not cover the first passages, thereby defining a second balloon cavity between the second balloon and the outer surface. A catheter sheath surrounds at least a portion of the catheter body for introduction of the distal segment into a body cavity (in the particular of the method of this invention the mediastinum of the thoracic cavity) and for extension of the first and second balloons beyond the distal extremity of the sheath for disposition of the exterior portion of the bag against the body part (pericardium), whereby a liquid introduced into the first lumen passes therethrough into the bag for inflation thereof and passage from the bag cavity through the outlets, and gas introduced through the second lumen passes therethrough into the second balloon for inflation thereof to expand against a portion of the anatomy of the mammal within the body cavity adjacent the body part (in the particular of the method of this invention, the mediastinum), thereby to press the exterior portion of the bag against the body part surface (the pericardium) so that liquid emerging from the outlets contacts the (pericardium) surface for (transpericardial) passage of the solute (nitrovasodilator) therethrough.

An apparatus in accordance with our invention for distribution of a gas (in a particular in accordance with a method of our invention, nitric oxide gas) onto a surface of a mammal body part (more particularly in accordance with a method of our invention, a coronary artery) comprises an elongated catheter body having a proximal and distal segment, the body defining first and second lumens extending therethrough. The first lumen extends through the distal end of the catheter for receiving a guidewire therethrough. The second lumen extends to at least one opening connecting the second lumen to the exterior of the distal segment. A tube surrounding at least a portion of the catheter body creates a passageway therebetween. A balloon comprising a gas permeable membrane is mounted to an outer surface of the distal segment of the body, thereby defining a balloon cavity between the balloon and the outer surface. A catheter sheath surrounds at least a portion of the catheter body for introduction of the distal segment into a body cavity and extension of the balloon beyond the distal extremity of the sheath for disposition exteriorly of the sheath on a guidewire. Accordingly, a gas introduced into the passageway passes therethrough into the balloon for inflation thereof and passes from the balloon cavity through the gas permeable membrane into contact with the body part (coronary artery), and gas within the balloon exits the balloon through the opening for withdrawal from the balloon

BRIEF DESCRIPTION OF THE DRAWINGS

The present invention may be more completely and easily understood when taken in conjunction with the accompanying drawings, in which.

DETAILED DESCRIPTION OF THE PREFERRED EMBODIMENT

Our invention involves a method of treating blood vessels in a mammal, which comprises the extravascular administration, adjacent and site-specific to a blood vessel in the mammal, especially a human, of a bioactive agent capable of one or more of the effects of (a) lysis of a platelet thrombus with restoration of blood flow, (b) inhibition of platelet adhesion and aggregation at the site(s) of vessel injury, and (c) vasodilation of the vessel at the injury site(s) to maintain blood flow through the vessel, at a dosage rate effective to promote the desired local therapeutic effect upon the vessel at the vessel injury site(s), but less than sufficient to generalize these effects systemically. The bioactive agent preferably is a conager of an endothelium-derived bioactive agent, including nitric oxide, sodium nitroprusside, nitroglycerin and prostacyclin. The method of administration includes controlled delivery of the bioactive agent over a sustained period of time. Typically, the site-specific dosage rate is significantly lower than a systemic dosage rate necessary to promote the therapeutic effects at the site(s).

When the bioactive agent is sodium nitroprusside and the site of blood vessel treatment is the site of endothelial injury and thrombus formation, the therapeutic effect is lysis of the thrombus with restoration of blood flow, inhibition of platelet aggregation adjacent to the injury site(s) without promoting systemic anticoagulation, and vasodilation adjacent to the site(s) to maintain blood flow through the vessel without promoting systemic hypotension. The method is also effective to promote vasodilation and prevent platelet thrombus formation, as where the site is the site(s) of a surgical procedure that injures the vessel, such as a PTCA procedure or a CABG operation. Thus the method is effective for treating acute thrombosis and chronic restenosis. When the bioactive agent is sodium nitroprusside administered extravascularly and adjacent to the treatment site(s), a dosage rate of from about 0.1 to about 3.0 μg/kg/min is effective to produce at least one of the desired therapeutic effects.

Figure 1:
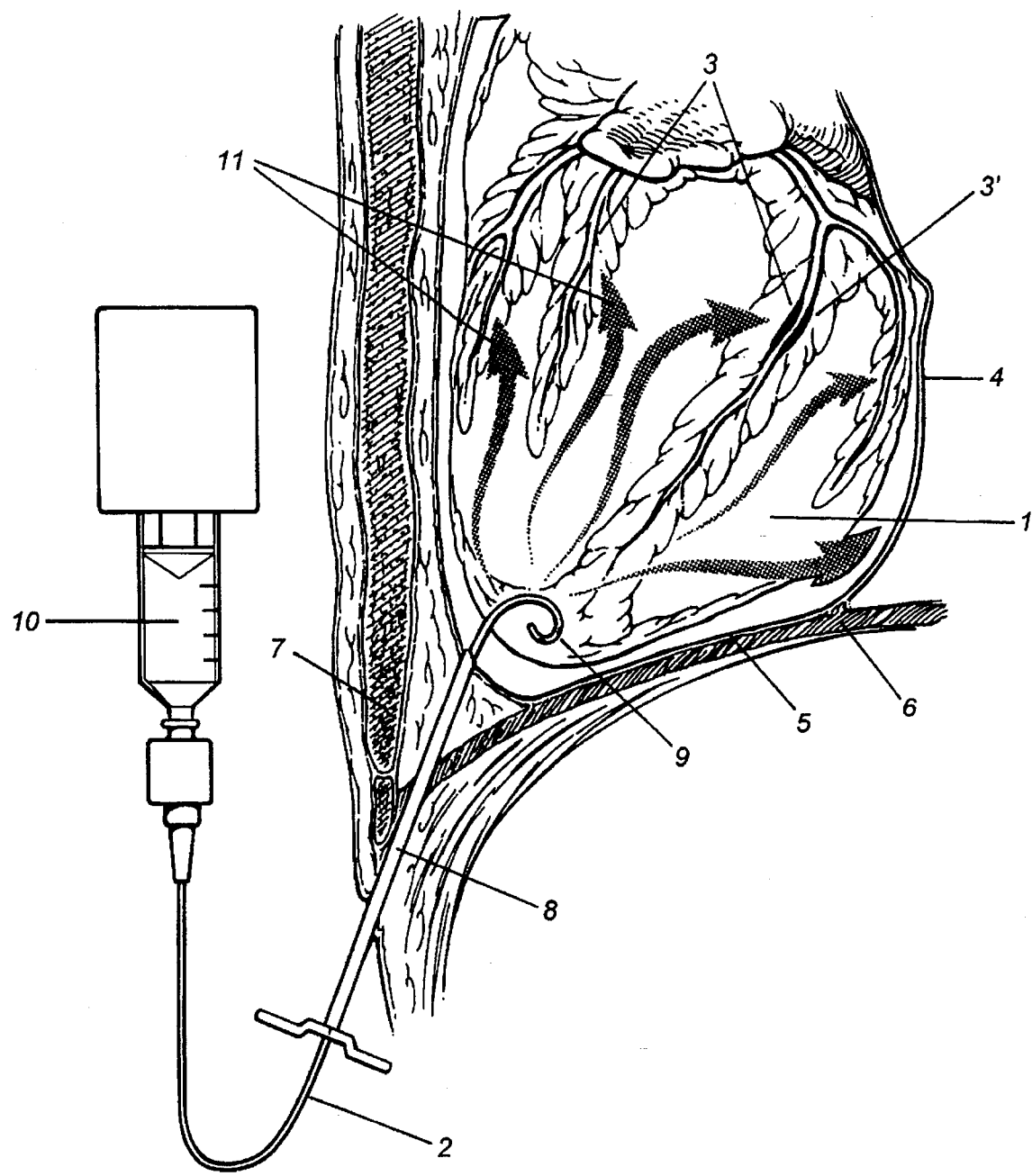
FIG. 1 is an illustration of the heart and a percutaneously inserted intrapericardial drug infusion catheter for intrapericardial delivery of nitrovasodilator to epicardial coronary arteries in accordance with this invention.

The method of administration includes infusion of the bioactive agent extravascular and adjacent the vessel at the specific site(s). In a preferred application, the vessel treated is a coronary blood vessel and bioactive agent delivery is by an infusion catheter, the distal outlet of which is percutaneously introduced into the pericardial sac surrounding the heart of the mammal. Preferably the distal outlet is of small size, suitably less than 1.5 mm in outer diameter, is made of a material that is nonreactive to adjacent tissues, suitably a silicone rubber polymer, is nontraumatic to adjacent tissues, suitably a 'pig-tail' tip design, and is effective for distributing the bioactive agent at the treatment site onto the extravascular surface of the target vessel(s). Referring now to FIG. 1, there is illustrated a the human heart 1 showing the epicardial coronary arteries 3, the pericardial sac 4 enveloping the heart, and pericardial fluid 5 bathing the heart within the pericardial sac. One of the coronary arteries 3 is indicated to be stenosed at 3'. Below the heart is the diaphragm musculature 6. In the chest of the patient in front of the heart is the sternum 7 and the lower extension thereof called the xiphoid process. Shown percutaneously inserted below the xiphoid process is a subxiphoid introducer 8 which has pierced the pericardium 4. Carried within the subxiphoid introducer 8 is a thereby percutaneously inserted intrapericardial nitrovasodilator agent infusion catheter 2. Catheter 2 includes a catheter pig-tail 9 which secures infusion catheter 2 within pericardium 4, and has one or more distal side holes indicated on both sides of the lead line of reference numeral "9" for delivery of the infused nitrovasodilator agent. Fluidly connected to the end of infusion catheter 2 external to the chest is external drug infusion pump 10 for delivery of nitrovasodilator agent intrapericardially and extravascularly to the epicardial coronary arteries 3, as indicated schematically by the arrows 11. The nitrovasodilator agent forms part of the bath in which the heart is bathed and the nitrovasodilator agent is delivered extravascularly, that is, to the outside of the vessels, for outside-in diffusion into the vessels.

Figure 2:
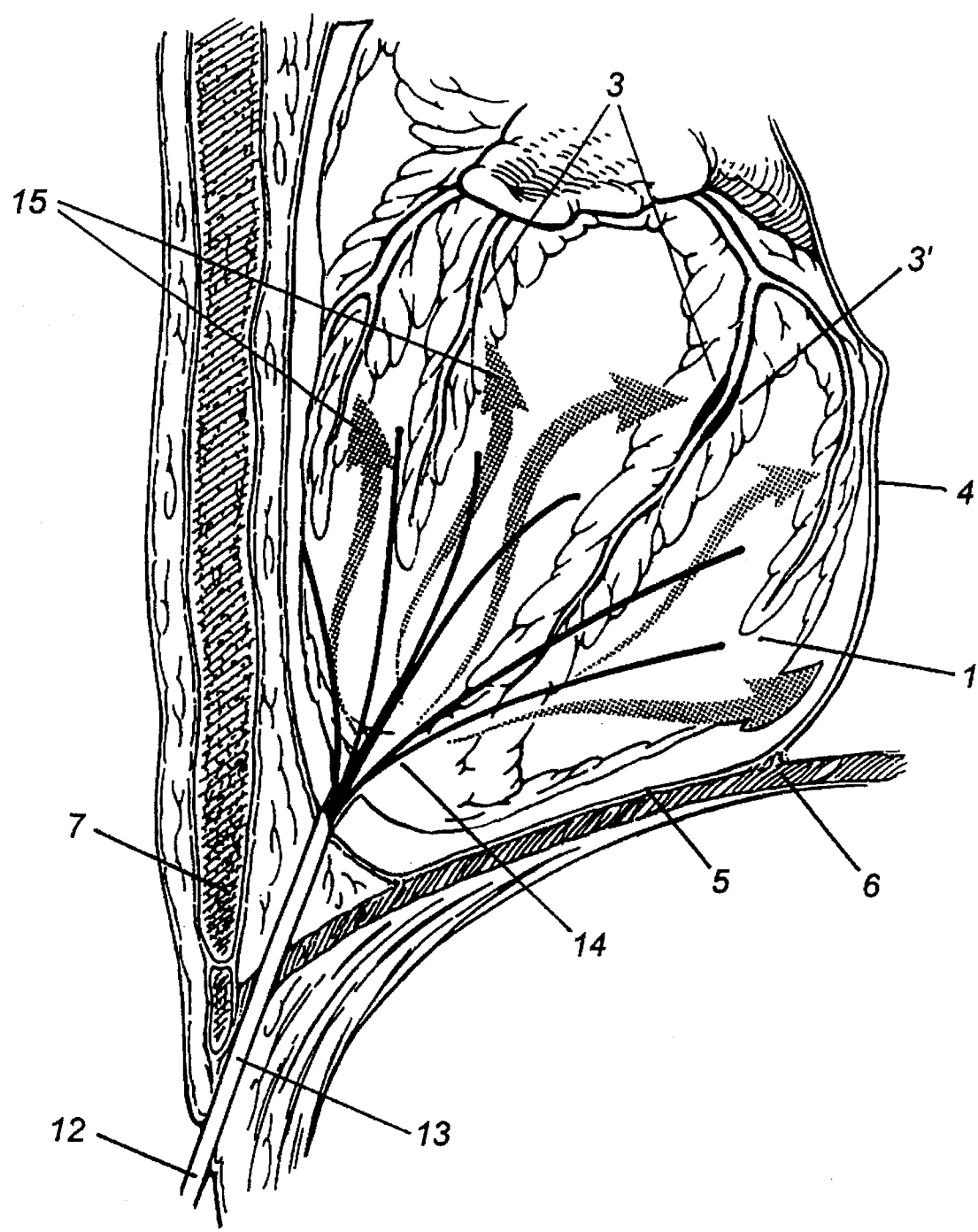
FIG. 2 is an illustration of the heart and a percutaneously inserted intrapericardial drug delivery implant for intrapericardial delivery of nitrovasodilator to epicardial coronary arteries in accordance with this invention.

The method of administration includes percutaneously or surgically inserting, extravascularly and adjacent the vessel at the site of treatment, an implant capable of extended time controlled-release of the bioactive agent. Preferably the implant includes a biodegradable polymer comprising the bioactive agent with controlled-release properties (see, for example, U.S. Pat. No. 5,099,060 and U.S. Pat. No. 4,980,449, incorporated herein by reference). The implant may be fiber-tipped for distribution of the bioactive agent to the treatment site from the biodegradable fiber tips. Referring to FIG. 2, an implant is illustrated. A heart 1 as in FIG. 1 has epicardial coronary arteries 3, pericardial sac 4, pericardial fluid 5, diaphragm 6 and sternum 7. One of the coronary arteries 3 is indicated to be stenosed at 3'. Shown percutaneously inserted below the xiphoid process of sternum 7 is a subxiphoid implant introducer 13, which has pierced the pericardium 4. Carried with in the implant introducer 13 is a thereby percutaneously inserted intrapericardial nitrovasodilator agent delivery implant 12 comprising nitrovasodilator agent/biodegradable polymer implant fibers 14 for intrapericardial release of nitrovasodilator from the erodible polymer extravascularly to the epicardial coronary arteries 3, as indicated schematically by the arrows 15. Suitable other forms of an implant for percutaneous pericardial extravascular insertion are intrapericardial microparticles and a sponge matrix, all comprising a biodegradable polymer.

Figure 3:
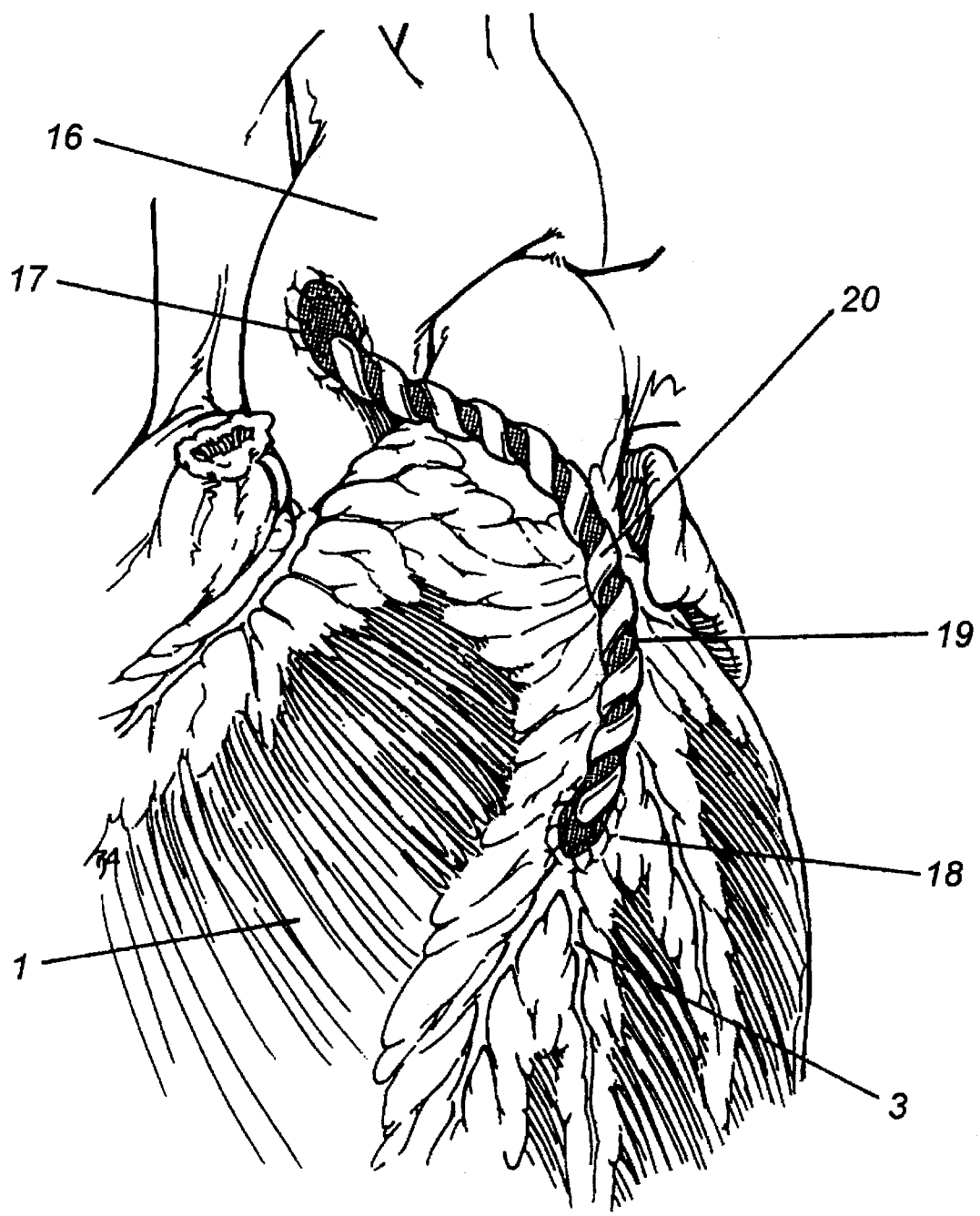
FIG. 3 is an illustration of the heart with coronary artery bypass vein graft and an extravascular biodegradable polymer spiral-wrap implant for controlled release of nitrovasodilator to the vein graft in accordance with this invention.

The implant suitably may comprise a wrap for a blood vessel at the site of treatment, the wrap comprising the bioactive agent. In a method of the invention directed to venous bypass graft treatment, the method of administration comprises surgically inserting around the vein graft an implant capable of extended controlled-release of the bioactive agent. A suitable form of the implant for extravascular insertion is a spiral-wrap device comprising a biodegradable polymer. Preferably the spiral-wrap implant is of a calibrated inner diameter, suitably to prevent vein graft distention, and is isocompliant with the vein graft, suitably to match normal coronary artery compliance. Referring to FIG. 3 is an illustration of the heart 1 showing the aorta 16, an epicardial coronary artery 3, a proximal anastomosis site 17 and a distal anastomosis site 18 of a coronary artery bypass vein graft 19, and an extravascular biodegradable polymer spiral-wrap implant for controlled release of nitrovasodilator drug to the vein graft 20.

Referring to FIGS. 10–13, an epipericardial drug distributing catheter apparatus 30 is illustrated for distribution of a liquid carrying a nitrovasodilator onto the pericardium for transpericardial delivery of the nitrovasodilator. The apparatus comprises an elongated catheter body or member 31 having a proximal segment 32 and distal segment 33. A first lumen 34 and second lumen 35 extend through body 31. First lumen 34 extends into a plurality of first passages 36 connecting first lumen 34 to a portion 37 of the exterior of distal segment 33. Second lumen 35 extends into a plurality of second passages 38 connecting second lumen 35 to a portion 39 of the distal segment exterior. A predominately laterally expandable bag 40 is mounted to an outer surface 41 of distal segment 33 to envelop and be free over the first passages 36 and not envelope and cover the second passages 38, thereby defining a bag cavity 42 between the bag 40 and the outer surface 41. Bag 40 has a plurality of fluid outlets 43 from balloon cavity 42 to an exterior portion 44 of bag 40, providing fluid communication from first lumen 34 to exterior portion 44. A predominately vertically expandable balloon 45 is mounted to an outer surface 46 of distal segment 33 to be free over second passages 38 and not cover first passages 36, thereby defining a balloon cavity 48 between balloon 45 and outer surface 46. A catheter sheath 47 surrounds catheter body 31.

Figure 10:
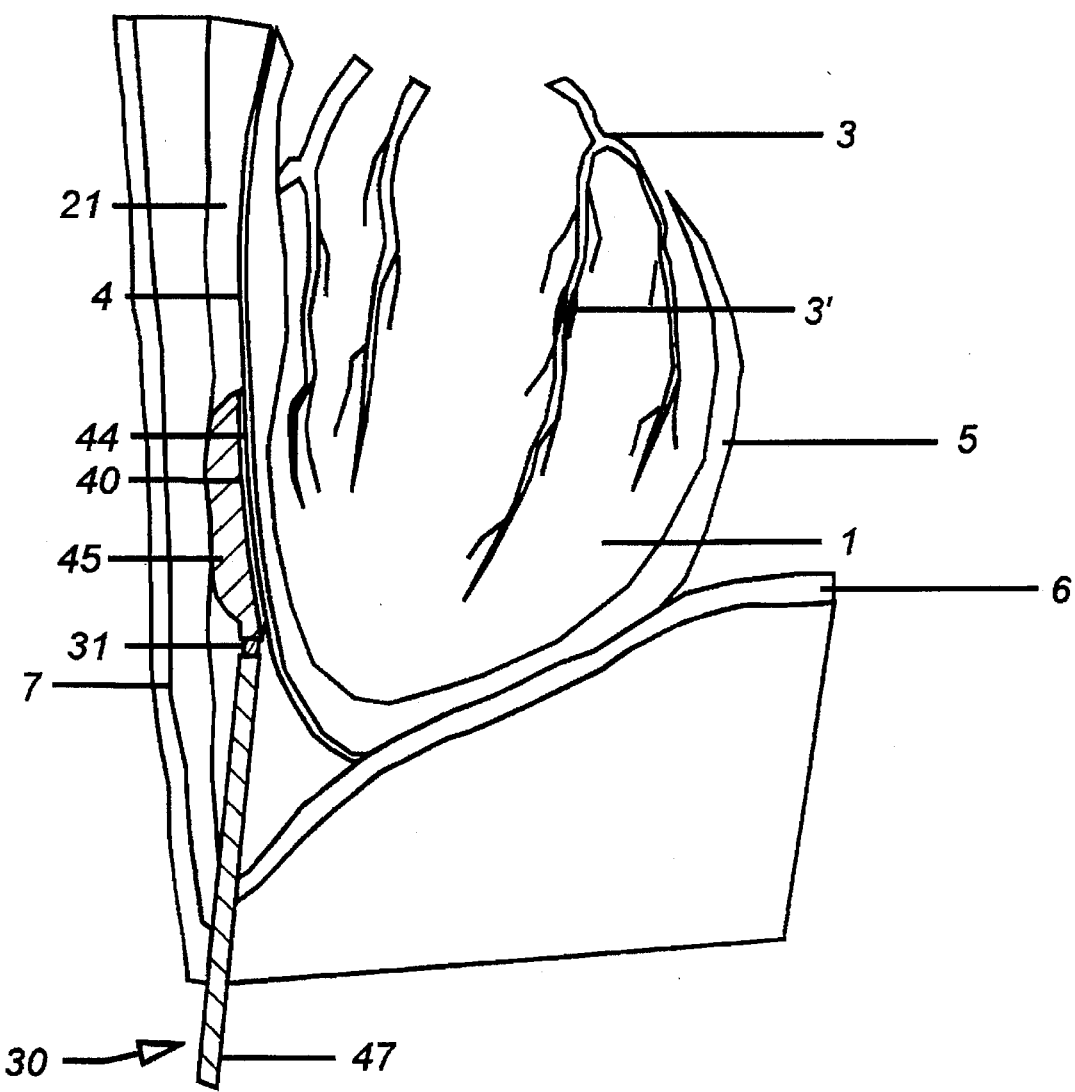
FIG. 10 schematically shows a transpericardial nitrovasodilator drug delivery catheter in place for use in accordance with this invention.
Figure 11:
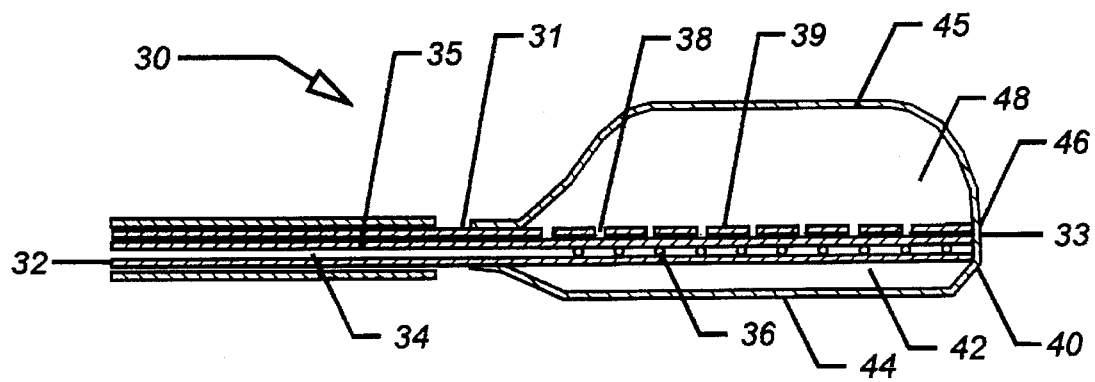
FIG. 11 schematically shows a longitudinal section of a portion of the transpericardial nitrovasodilator drug delivery catheter of FIG. 10.
Figure 12:
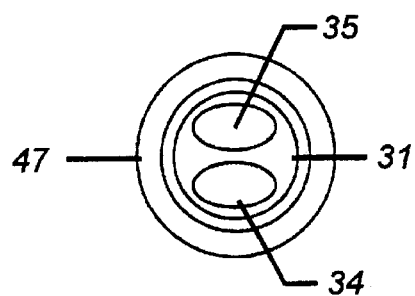
FIG. 12 schematically shows a cross section of the portion of the transpericardial nitrovasodilator drug delivery catheter of FIG. 11.
Figure 13:
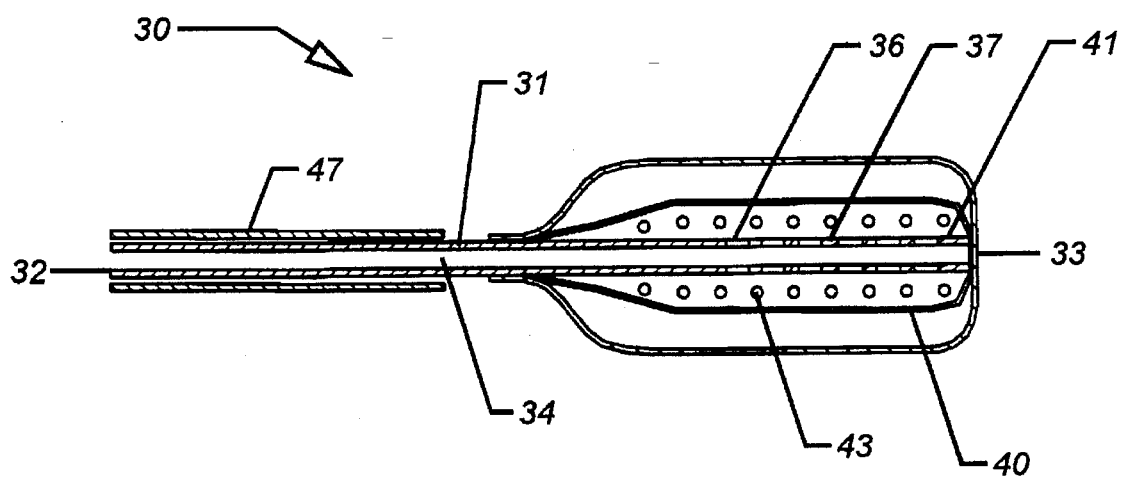
FIG. 13 schematically shows a bottom view of a distal portion of the transpericardial nitrovasodilator drug delivery catheter of FIG. 10.

In use of drug delivery catheter 30, sheath 47 with catheter 31 nested therein is advanced within an introducer under the xiphod process of the sternum 7 into the mediastinum 21 of the thoracic cavity 22 to a position between pericardium 4 and the inner chest wall, as shown in FIG. 10. The distal end of catheter body 31 is advanced from sheath 47 to extend the first and second balloons 40 and 45 beyond the distal extremity of the sheath and dispose exterior portion 44 of bag 40 against pericardium 4 and orient second balloon 45 facing the inner chest wall. A gas, suitably air, is introduced through second lumen 35 and passes therethrough into second balloon 45, inflating balloon 45 predominately vertically, relative to the axis of the elongate catheter body 31. This expands balloon 45 into contact against the inner chest wall of the mediastinum. Further inflation causes balloon 45 to press exterior portion 44 of bag 40 against the surface of pericardium 7. A liquid is introduced into first lumen 34 and passes therethrough into bag 40, expanding bag 40 predominately laterally. The liquid passes from bag chamber or cavity 42 through the outlets 43 and emerges therefrom onto the surface of pericardium 4 for transpericardial passage of a drug (nitrovasodilator) in solution in the liquid and entry of the drug into the pericardial fluid bathing the heart, from which it comes into contact with the coronary arteries for migration into the vessel wall.

Figure 14:
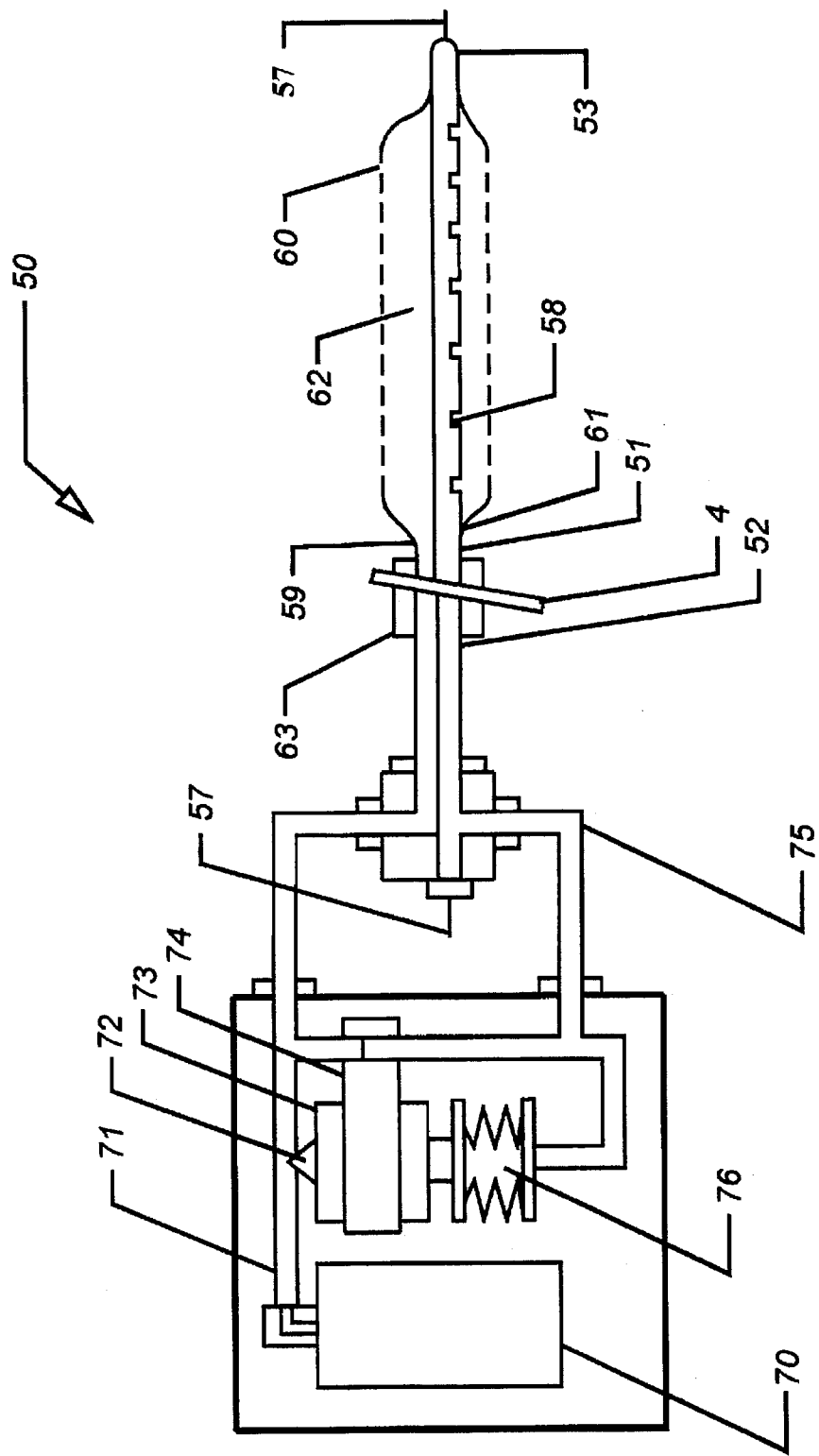
FIG. 14 schematically shows a longitudinal section of an intrapericardial nitrovasodilator drug delivery catheter for delivery of gaseous nitric oxide to epicardial coronary arteries in accordance with this invention, schematically connected with a gas supply and control system.
Figure 15:
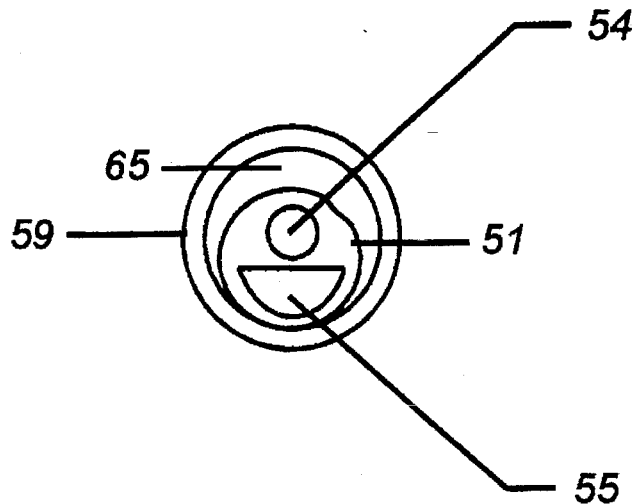
FIG. 15 schematically shows a cross section of a proximal part of the intrapericardial nitrovasodilator drug delivery catheter of FIG. 14.
Figure 16:
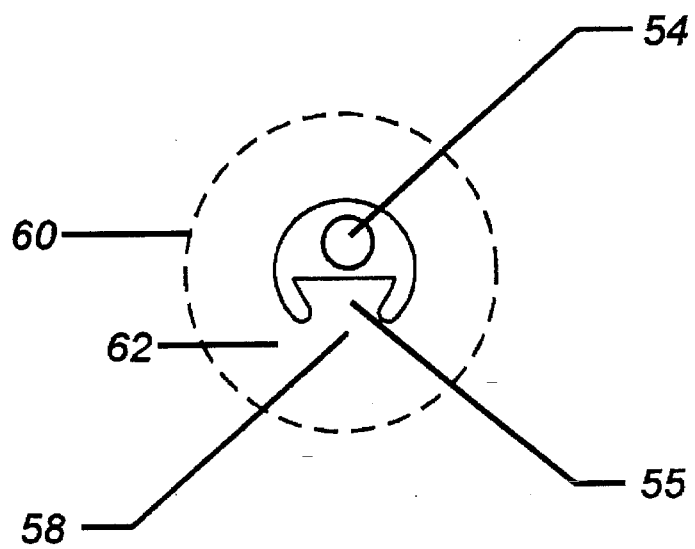
FIG. 16 schematically shows a cross section of a distal part of the intrapericardial nitrovasodilator drug delivery catheter of FIG. 14.

Referring to FIGS. 14–16, an apparatus 50 for intrapericardial delivery of gaseous nitric oxide to the epicardial coronary arteries in accordance with our invention is illustrated schematically. Apparatus 50 comprises an elongated catheter body 51 having a proximal segment 52 and a distal segment 53, body 51 defining a first lumen 54 and a second lumen 55 extending therethrough. First lumen 54 extends through the distal end 53 of catheter 51 for receiving a guidewire 57 therethrough. Second lumen 55 extends to at least one opening 58 (a plurality of openings 58 are illustrated in this embodiment). Openings 58 connect second lumen 55 to the exterior of distal segment 53. A tube 59 surrounding at least a portion of catheter body 51 creates a passageway 65 therebetween. A balloon 60 comprising a gas permeable membrane is mounted to an outer surface 61 of the distal segment of body 51, thereby defining a balloon cavity 62 between balloon 60 and body 51. An introducer 63 surrounds at least a portion of catheter body 51 for introduction of distal segment 53 into the thoracic cavity and extension of balloon 60 beyond the distal extremity of sheath 63 for disposition exteriorly of the sheath on guidewire 57.

In use of apparatus 50 for intrapericardial delivery of gaseous nitric oxide to the epicardial coronary arteries in accordance with our invention, gaseous nitric oxide supplied by tank 70 is carried by conduit 71 controlled by microvalve 72 actuated by a solenoid 73 responsive to a pressure differential diaphragm 74 and is introduced into catheter apparatus 50, of which distal segment 53 has been introduced through the pericardium 4 through introducer 63. The nitric oxide gas flows through passageway 65 and passes into balloon 60 which it inflates. The nitric oxide resident in balloon cavity 62 passes from cavity 62 through the gas permeable membrane of balloon 60 and enters the pericardial fluid bathing the coronary arteries for treatment of them. Gas within balloon cavity 62 has an exit passage from balloon cavity 62 through openings 58 for withdrawal from the balloon through lumen 55 into a gas return conduit 75 under the force of withdrawal pump 76.

Figure 17:
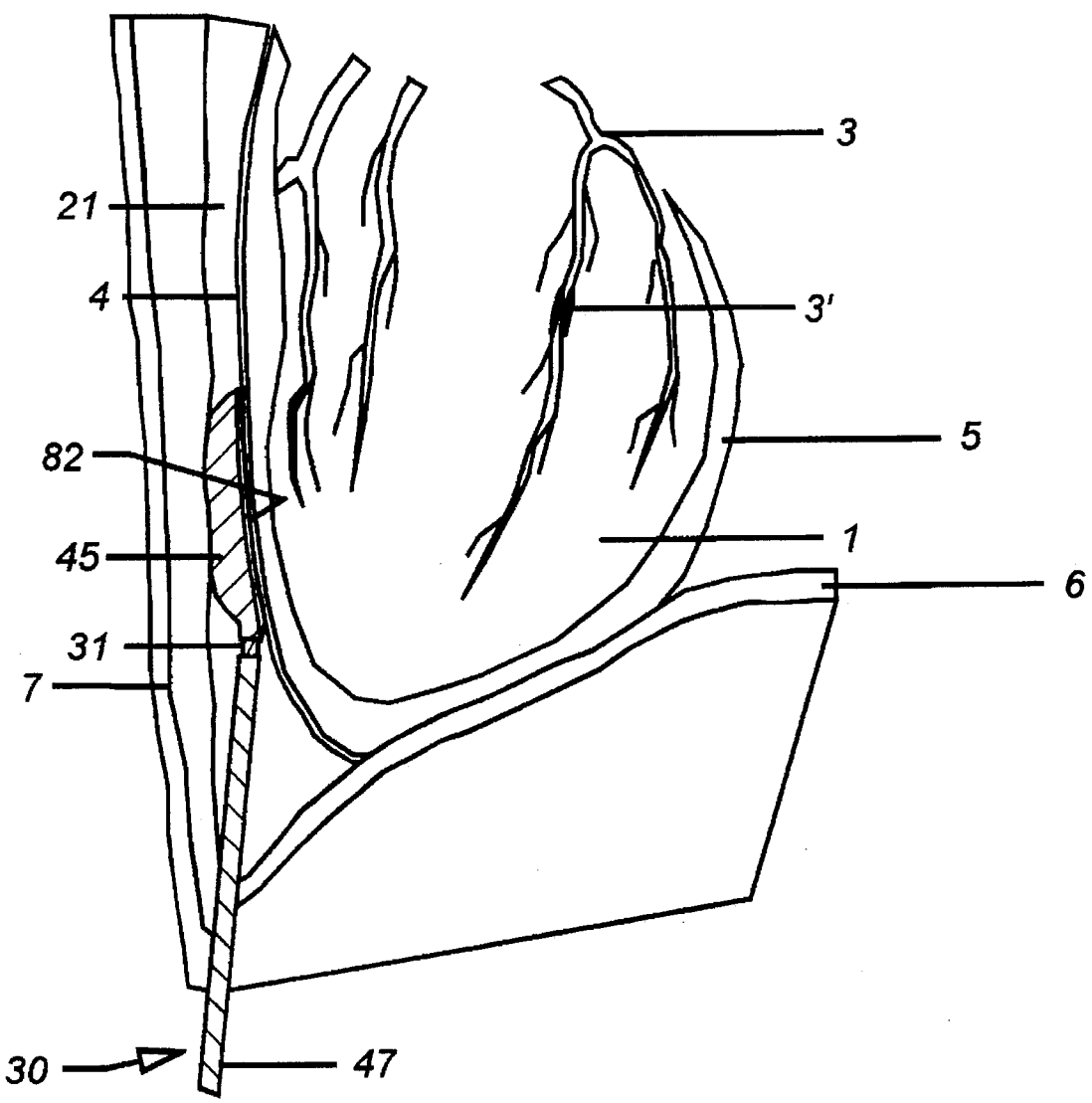
FIG. 17 schematically shows an iontophoretic transpericardial nitrovasodilator drug delivery catheter in place for use in accordance with this invention.
Figure 18:
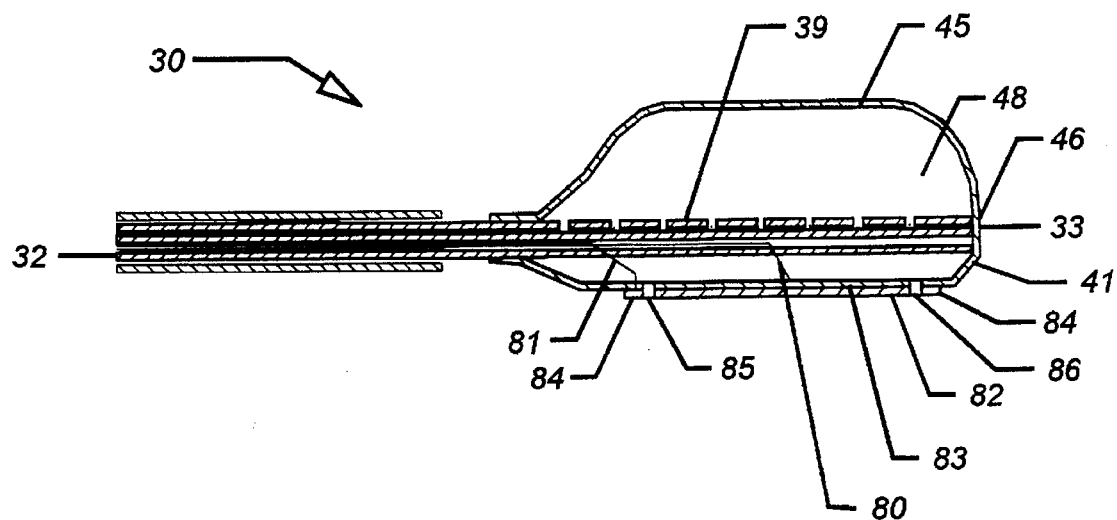
FIG. 18 schematically shows a longitudinal section of a portion of the iontophoretic transpericardial nitrovasodilator drug delivery catheter of FIG. 17.
Figure 19:
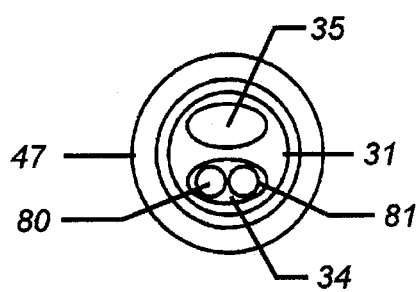
FIG. 19 schematically shows a cross section of the portion of the iontophoretic transpericardial nitrovasodilator drug delivery catheter of FIG. 17.

Referring to FIGS. 17–19, an apparatus for iontophoretic delivery of a nitrovasodilator onto the pericardium for transpericardial delivery of the nitrovasodilator is depicted schematically. The device is similar to the device illustrated in FIGS. 10–12, and corresponding numbers indicate similar structure, except the first lumen 34 does not lead to passages connecting the lumen exteriorly into a balloon cavity. Instead, lumen 34 (see FIG. 19) carries electrical leads 80, 81. Voltage carrying lead 80 is connected to a charge plate 83 in front of which is a pad 82 containing a repository of a nitrovasodilator. Pad 82 is attached to the outer surface 41 of distal segment 33. Circumscribing the perimetry of pad 82 is negative electrode 84, electrically insulated from charge plate 83 and pad 82 by electrode insulators 85, 86. Negative electrode 84 is coupled to the ground of lead 81. When pad 82 is placed in contact with the pericardium 4 and plate 83, a charge is provided over lead 80 to charge plate 83. An electric field is established between charge plate 83 and negative electrode 84. This electric field penetrates through the pericardium as it flows from plate 83 to electrode 84. The field passes through nitrovasodilator pad 82, and charged nitrovasodilator molecules contained within pad 82 migrate from pad 82 and through pericardium 4 as the electric field traverses the pericardial membrane. The charge supplied to plate 83 is sufficient to establish the iontophoretic circuit, but insufficient to disturb the transmission of the cardiac impulse through the heart.

In the following examples, the method of this invention is demonstrated to be effective.

EXAMPLE 1

Materials And Methods

All procedures in this an the following examples were conducted according to the principles of the American Physiological Society.

Twenty mongrel dogs weighing 25–35 kg were anesthetized with sodium pentobarbital (30 mg/kg given intravenously) and connected to a mechanical ventilator. Plastic catheters were placed in the left carotid artery for monitoring blood pressures and in a cephalic vein for administering fluids and drugs. A balloon-tipped thermodilution catheter was placed through a jugular vein into the pulmonary artery for measuring pulmonary artery pressure and cardiac output. A left thoracotomy was performed in the fifth intercostal space, and the heart was exposed through a small pericardial window. A plastic cuff was fixed to the edge of the incised pericardium to prevent the leakage of fluid from the pericardial sac, thus creating a pericardial well. A 1–2 cm segment of the left anterior descending (LAD) coronary artery was carefully exposed by dissection and nearby vessel branches were ligated. A miniature ultrasonic Doppler flow probe was placed around the proximal part of the exposed LAD coronary artery to measure the velocity of blood flow. An additional plastic catheter was positioned in the coronary sinus for collecting venous blood samples from the coronary circulation.

Basic hemodynamics were continuously recorded on a physiologic recorder, including heart rate, systolic and diastolic aortic blood pressures, systolic, diastolic, and balloon-wedge pulmonary artery pressures, phasic and mean blood flow velocities in the LAD coronary artery, and thermodilution cardiac output.

The endothelium of the LAD coronary artery was injured by squeezing the artery 10–20 times with cushioned forceps. A plastic constrictor was placed around the LAD coronary artery at the site of injury to occlude the vessel and reduce the phasic flow velocity to approximately 60% of the baseline level. Subsequently, cyclic flow reductions (CFR's) developed as a result of recurrent platelet adhesion, aggregation and dislodgement on the injured endothelial surface. These 20 dogs were further studied in three groups:

Group I. In six dogs, saline was dripped onto the surface of the exposed LAD coronary artery and into the pericardial well at a infusion rate of 0.2 ml/min through a plastic catheter. The saline infusion was continued for 60 minutes and hemodynamics were recorded continuously. The animals were then humanely killed by pentobarbital overdose.

Group II. In seven dogs, sodium nitroprusside (Abbott Labs, North Chicago, Ill.) was administered via delivery catheter on the extravascular surface of the injured LAD coronary artery and allowed to accumulate in the pericardial well. The intrapericardial dose of sodium nitroprusside was started at 0.5 µg/kg/min. If CFR's were not affected within 30 minutes, the dosage was increased to 3.0 µg/kg/min. A maximal dosage of 6.0 µg/kg/min was given to the animals not responding to the two lower doses. The animals were killed 30 minutes after CFR's were abolished or after the highest dose of sodium nitroprusside was given for 30 minutes in the manner described above.

Group III. In the remaining seven dogs, sodium nitroprusside was administered intravenously at the same dosage range described for Group II. The animals were monitored and killed in the same manner as described above.

Results

All values were expressed as the mean ± standard error of the mean. A one-way analysis of variance with repeated measurements was used to compare the frequency of CFR's and the hemodynamic changes obtained at different time periods before and after each treatment. Student's t-test was used compare values between two different groups ($p<0.05$ was considered significant).

1. Effect of Nitroprusside on CFR's

Cyclic coronary flow reductions developed in all 20 dogs after endothelial injury and the external constriction of the LAD coronary artery. The reduction of coronary flow velocity caused by external constriction was similar among the 3 experimental groups of animals (phasic flow velocity reduced to 70.7 ±9.2% of baseline in Group I, to 66.5±4.9% in Group II, and to 56.4 ±5.0% in Group III ($p>0.05$). The frequency of initial (baseline, no drug) cyclic flow reductions in the coronary arteries was also similar among the 3 groups of animals. The heart rate and aortic blood pressure did not change significantly after the development of CFR's. After 30 minutes of consistent CFR's, for all studies, different interventions were then administered.

In the Group I studies, intrapericardial infusion of saline did not change the flow pattern or CFR frequency in any of the 6 animals (0% effective).

Figure 4:
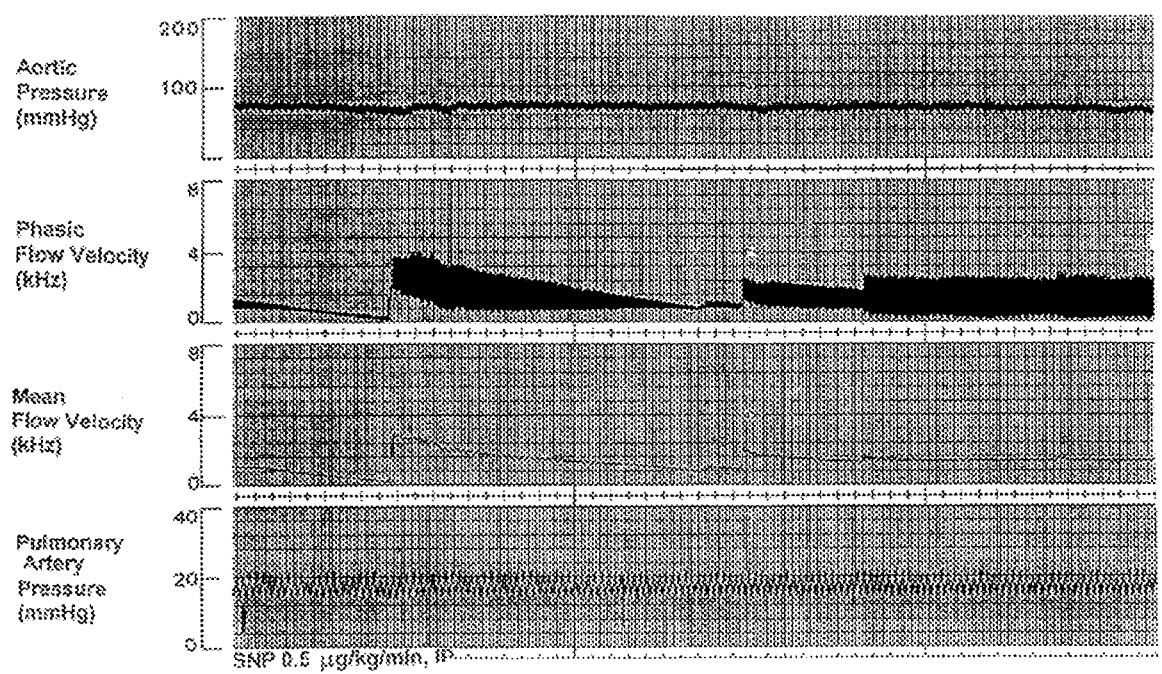
FIG. 4 is a representative recording of aortic pressure, phasic and mean flow velocity in the left anterior descending coronary artery, and pulmonary arterial pressure explained in Example 1.

In the Group II studies, intrapericardial infusion of sodium nitroprusside (FIG. 4) abolished the CFR's within 10 to 30 minutes in all 7 animals (100% effective).

In the Group III studies, intravenous infusion of sodium nitroprusside abolished the CFR's within 10 to 30 minutes in 5 of 7 animals (71% effective).

Figure 5A:
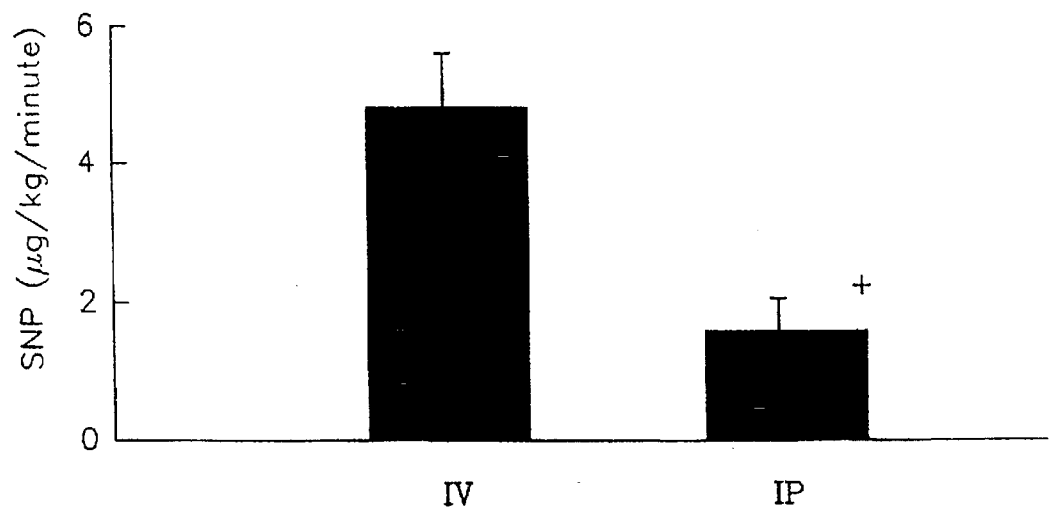
FIG. 5A shows dosage of sodium nitroprusside (SNP, µg/kg/min) required to abolish cyclic flow reductions given intravenously (IV) or intrapericardially (IP), as explained in Example 1.

As shown in FIG. 5A, the average dose of sodium nitroprusside required to abolish the CFR's was significantly lower when it was administered intrapericardially than when it was given intravenously (1.6±0.5 vs. 4.8±0.8 µg/kg/min, respectively). Referring to FIG. 5A, IP drug delivery compared to IV drug administration, +p<0.01.

Figure 5B:
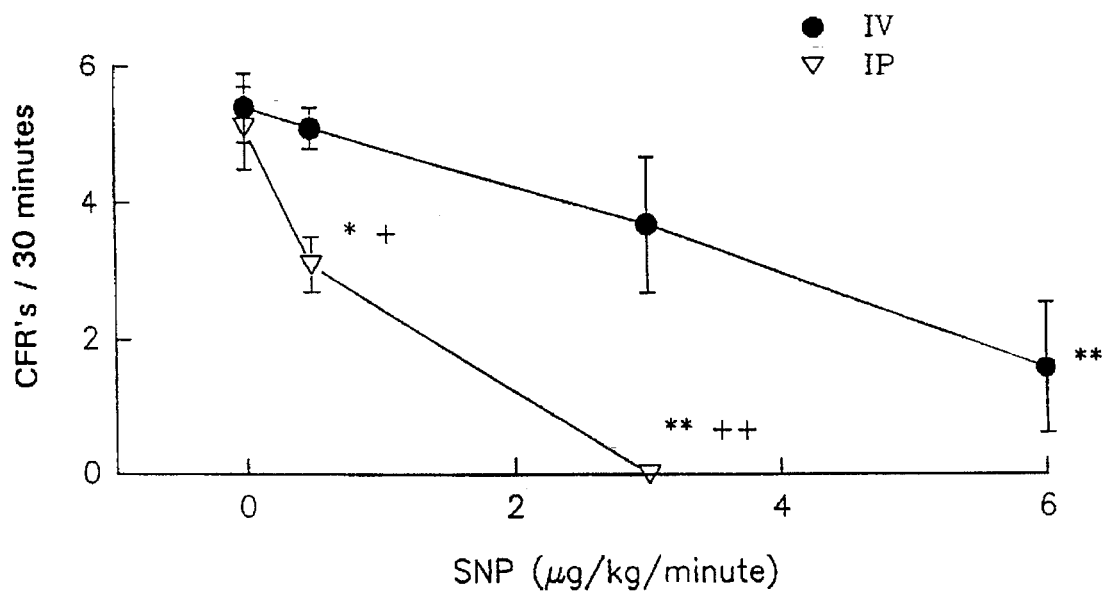
FIG. 5B shows change in frequency of cyclic flow reductions (CFR's/30 minutes) after each dose of sodium nitroprusside (SNP, μg/kg/min) given intravenously (IV) or intrapericardially (IP), as explained in Example 1.
Figure 6A:
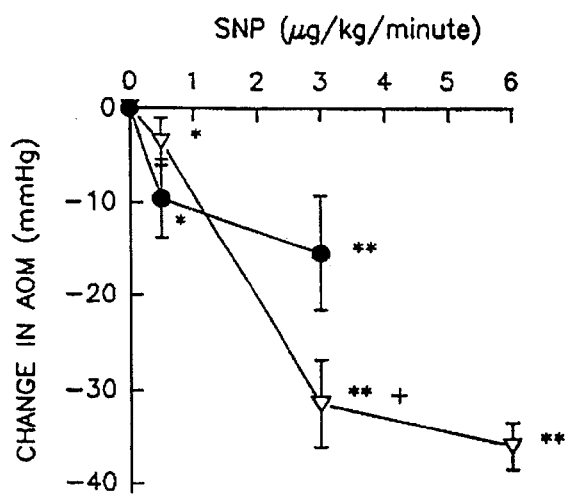
FIGS. 6A–6D show changes respectively in mean aortic pressure (AOM, mmHg), cardiac output (CO, L/min), peripheral vascular resistance (PVR, units), and pulmonary arterial pressure (PAP, mmHg) after each dose of sodium nitroprusside (SNP, μ/kg/min) given intrapericardially (IP) or intravenously (IV), as explained in Example 1.
Figure 6B:
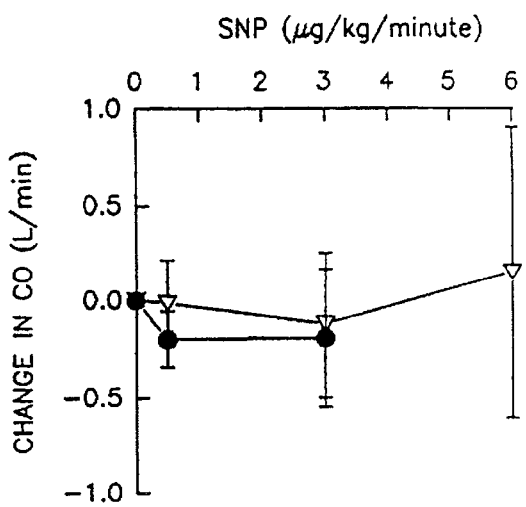
Figure 6C:
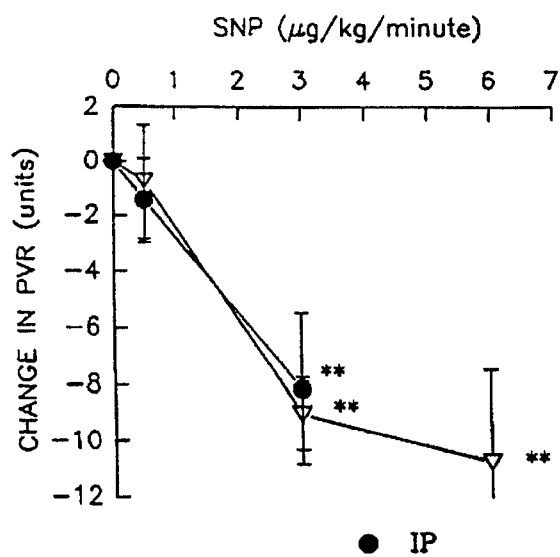
Figure 6D:
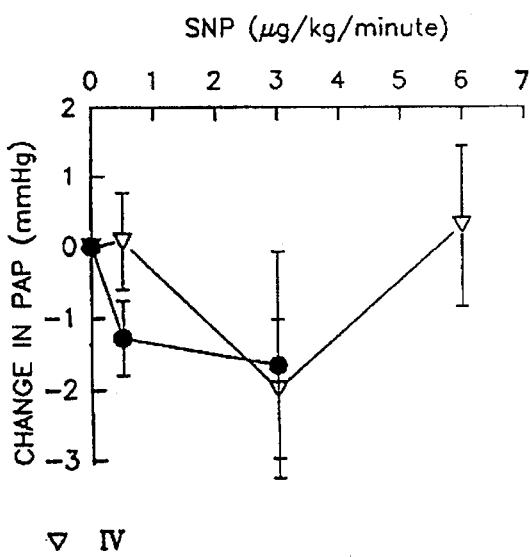

As shown in FIG. 5B, the frequency of CFR's was also significantly lower in animals that received intrapericardial sodium nitroprusside than in animals that received sodium nitroprusside at the same dose intravenously. Referring to FIG. 5B, compared to control values, *p<0.05, **p<0.01; compared to IV drug administration, p<0.05, ++p<0.01.

These data indicate that treatment with sodium nitroprusside protects against CFR's in stenosed and endothelium injured coronary arteries and that the effective dosage required to abolish CFR's is lower and more effective when it is given intrapericardially than when it is given intravenously.

2. Effect Of Nitroprusside On Hemodynamics

Intrapericardial saline infusion (Group I) did not significantly change aortic pressures, cardiac output, pulmonary artery pressures or peripheral vascular resistance. As shown in FIGS. 6A–6D, sodium nitroprusside infusion (Groups II and III) reduced aortic pressures and peripheral vascular resistance in a dose-dependent manner. Cardiac output and pulmonary artery pressures were not significantly affected by either intravenous or intrapericardial administration of sodium nitroprusside. Referring to FIGS. 6A–6D, compared to the control values, *p<0.05, **p<0.01; compared to IP at 3.0 µg/kg/min, +p<0.01.

These data indicate that extravascular intrapericardial infusion of sodium nitroprusside has an advantage over intravenous infusion in reducing the systemic hypotensive side-effects of sodium nitroprusside.

EXAMPLE 2

Effect Of Nitroprusside On Platelet Aggregation

Methods and Materials

Ex-vivo platelet aggregation was performed before and 10 minutes after the administration of each dose of sodium nitroprusside in Groups II and III. Blood samples were collected from the plastic catheters in the aorta and the coronary sinus and anticoagulated with 3.8% sodium titrate (9 volumes blood: 1 volume sodium citrate). Platelet-rich plasma was obtained by centrifuging the whole blood sample at 200x g for 20 minutes at room temperature. The platelet count in platelet-rich plasma was adjusted to 300, 000/mm$^3$. A four-channel platelet aggregometer (model PAP-4, Bio-Data, Horsham, Pa.) was used for the assay. Collagen (Sigma, St. Louis, Mo.) was used as a platelet agonist. The degree of platelet aggregation was reported as a percentage of maximal increase of light transmission in platelet-rich plasma over that in platelet-poor plasma.

Results

As in Example 1, all values were expressed as the mean ± standard error of the mean. A one-way analysis of variance with repeated measurements was used to compare the frequency of the platelet aggregation values obtained at different time periods before and after each treatment. Student's t-test was used compare values between two different groups ($p<0.05$ was considered significant).

Figure 7A:
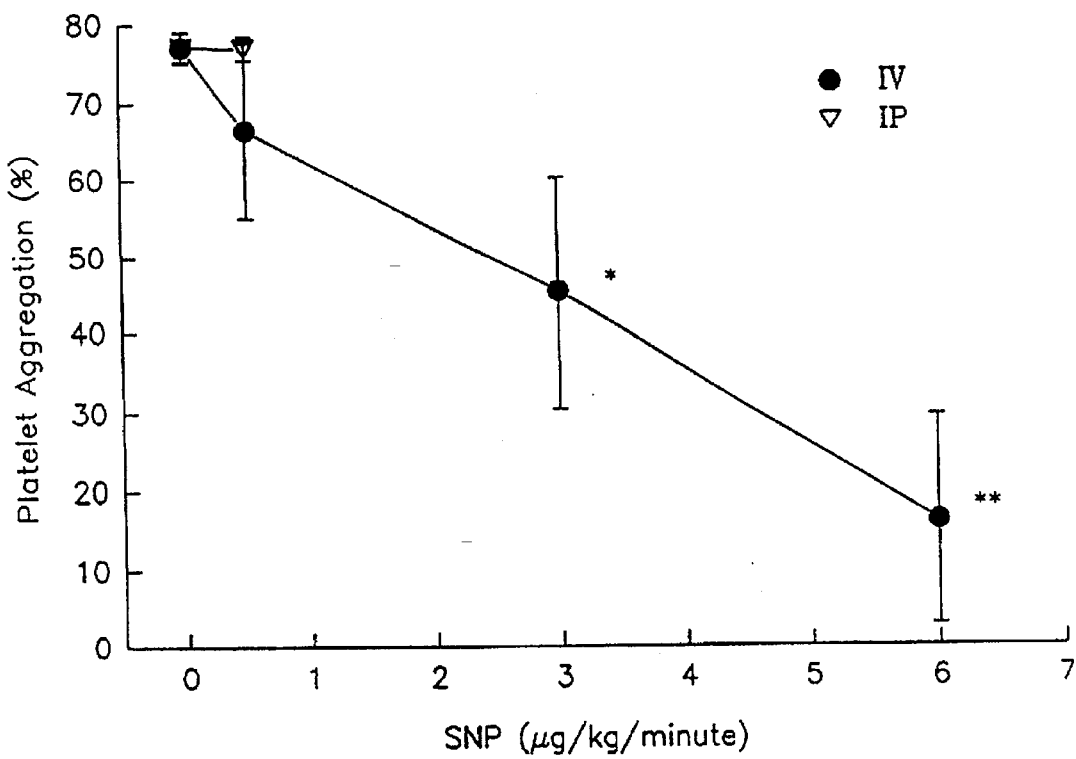
FIG. 7A shows percent change in ex-vivo platelet aggregation induced by collagen at 20 μg/ml in platelet-rich plasma obtained from systemic circulation before and after each dose of sodium nitroprusside (SNP, μg/kg/min) given intravenously (IV) or intrapericardially (IP), as explained in Example 2.
Figure 7B:
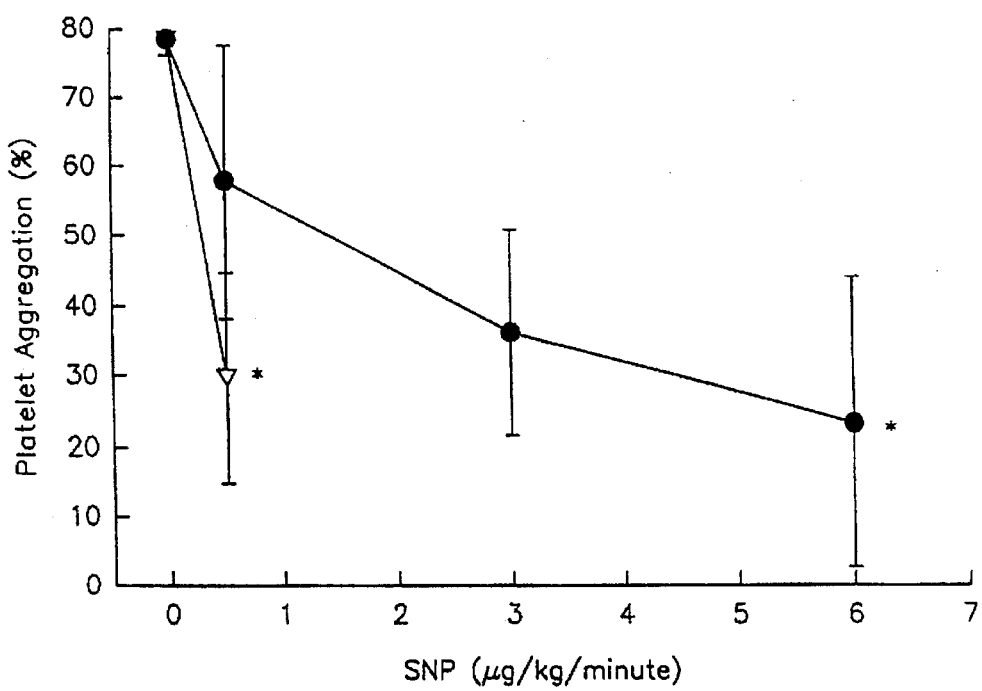
FIG. 7B shows percent change in ex-vivo platelet aggregation induced by collagen at 20 μg/ml in platelet-rich plasma obtained from coronary circulation (coronary sinus) before and after each dose of sodium nitroprusside (SNP, μg/kg/min) given intravenously (IV) or intrapericardially (IP), as explained in Example 2.

Sodium nitroprusside infusion (Groups II and III) inhibited collagen-induced platelet aggregation in a dose-dependent manner in both the systemic circulation (FIG. 7A, compared to control level, *p<0.05, **p<0.01) and coronary circulation (FIG. 7B, compared to control level, *p<0.05). In the animals treated with extravascular intrapericardial sodium nitroprusside, the degree of inhibition of platelet aggregation in coronary circulation was higher than that in the systemic circulation (FIG. 7B).

These data indicate that inhibition of platelet aggregation in the coronary circulation is greater with extravascular intrapericardial infusion of sodium nitroprusside than when it is given intravenously and reduces the systemic side-effects of antiplatelet therapy, such as bleeding complications.

EXAMPLE 3

Effect of Nitric Oxide on CFR's

Methods and Materials

This example was a study to determine the mechanisms involved in the action of sodium nitroprusside. The same preparative procedure was followed as in Example 1 for an additional group of five dogs (Group IV), except that in these animals, plastic catheters were also placed into the left atrium of the heart and into a branch of the LAD coronary artery proximal to the exposed segment. The exposed LAD coronary artery was mildly injured (3–5 vessel squeezes) and stenosed with a plastic constrictor. An inhibitor of nitric oxide synthetase, N$^G$-mono-methyl-L-arginine (L-NMMA, Calbiochem, La Jolla, Calif.), was administered into the left atrium at 5 mg/kg to eliminate the production of endogenous nitric oxide and induce CFR's. After 30 minutes of L-NMMA-induced CFR's, sodium nitroprusside was administered via delivery catheter on the extravascular surface of the injured LAD coronary artery and into the pericardial well. If the CFR's were abolished by the intrapericardial infusion of sodium nitroprusside, oxyhemoglobin, a scavenger of nitric oxide, was administered into the LAD coronary artery. Oxyhemoglobin was given at incremental doses of 200, 400, and 600 µg/kg/min. If oxyhemoglobin restored the CFR's abolished by intrapericardial sodium nitroprusside, the animals were monitored for 30 minutes to ensure the consistency of the CFR's and were then killed in the manner described above.

Results

As in the prior examples, all values were expressed as the mean ± standard error of the mean. A one-way analysis of variance with repeated measurements was used to compare the frequency of CFR's and the hemodynamic changes obtained at different time periods before and after each treatment. Student's t-test was used compare values between two different groups (p<0.05 was considered significant).

Figure 8:
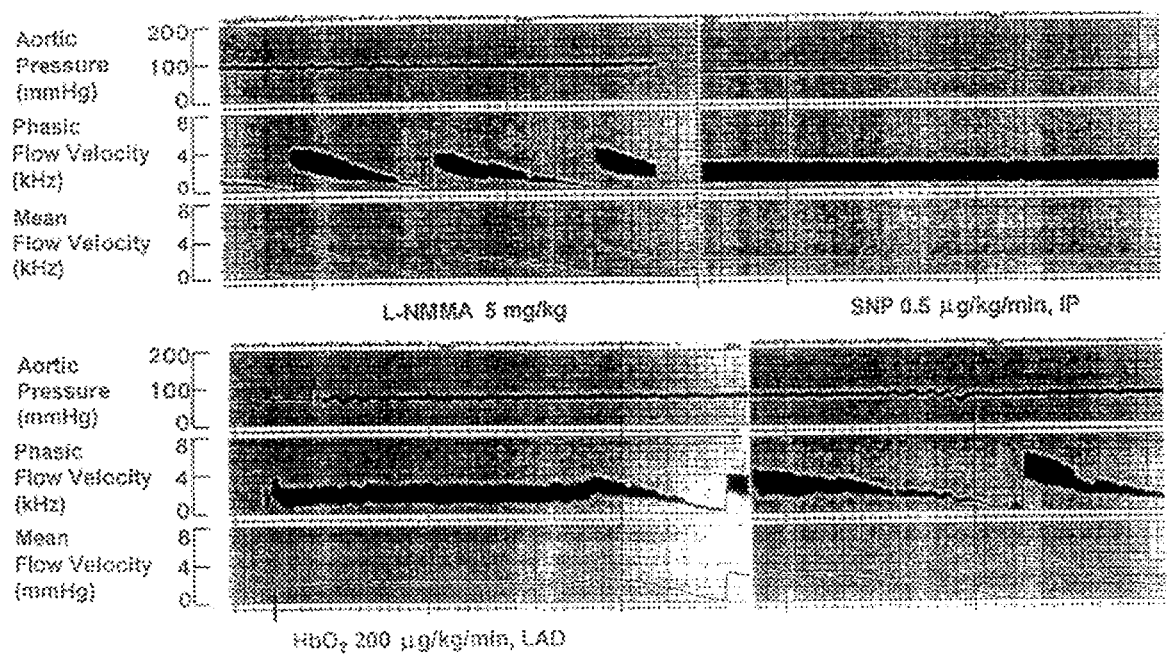
FIG. 8 is a representative recording of aortic pressure and phasic and mean flow velocity in the left anterior descending coronary artery (LAD) after $N^G$-monomethyl-L-arginine (L-NMMA) was given into the left atrium at 5 mg/kg, after sodium nitroprusside (SNP) was given intrapericardially at 0.5 μg/kg/min, and after oxyhemoglobin ($HbO_2$) was given into the LAD CORONARY ARTERY at 200 μg/kg/min, as explained in Example 3.
Figure 9:
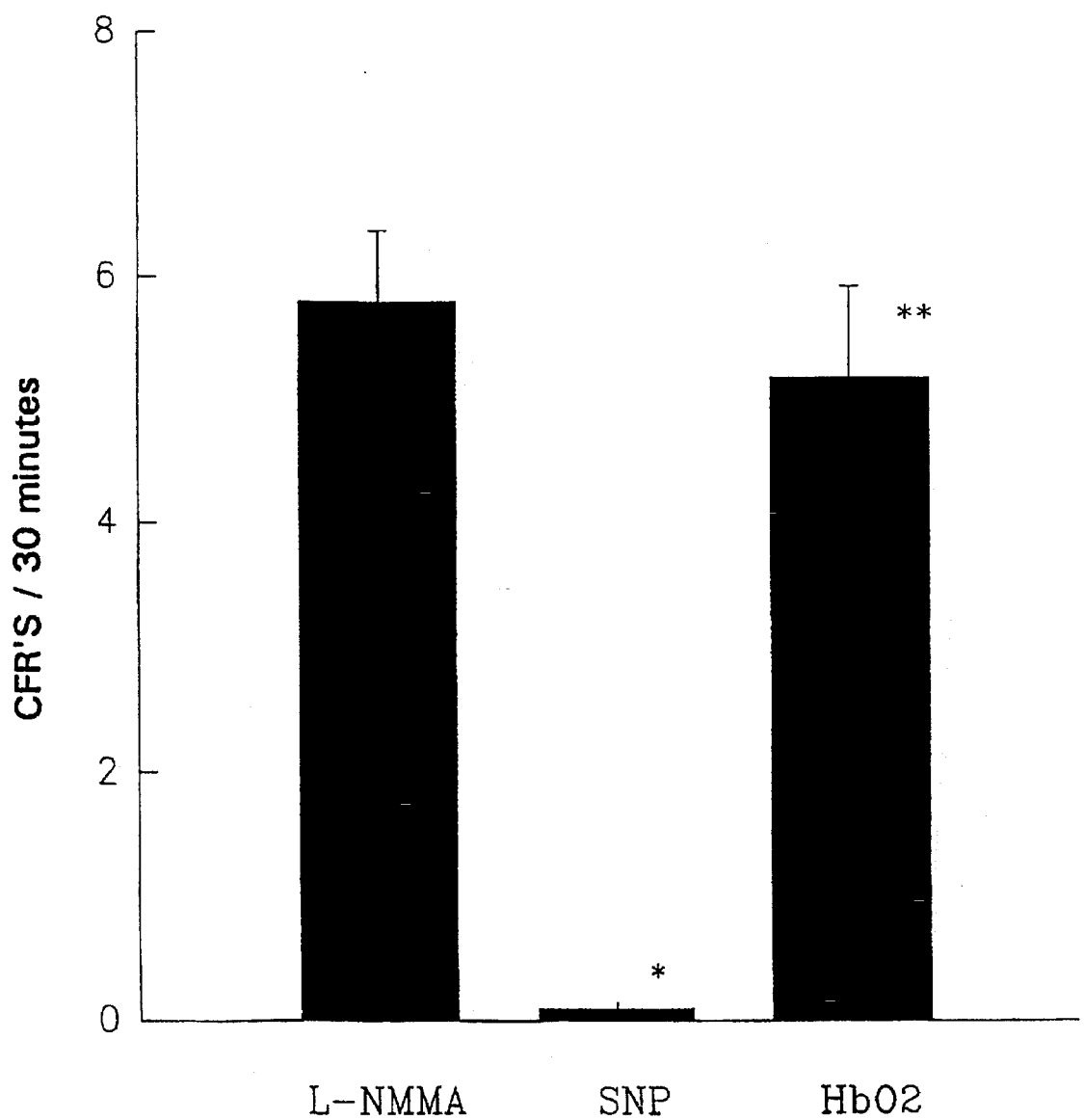
FIG. 9 shows changes in frequency of cyclic flow reductions (CFR's/30 minutes) in the left anterior descending coronary artery (LAD) after $N^G$-monomethyl-L-arginine (L-NMMA) was given into the left atrium at 5 mg/kg, after sodium nitroprusside (SNP) was given intrapericardially at 0.5 μg/kg/min, and after oxyhemoglobin ($HbO_2$) was given into the LAD coronary artery at 200–600 μg/kg/min., as explained in Example 3. Compared to L-NMMA, *p<0.01; compared to SNP, **p<0.01.

Infusion of L-NMMA into the left atrium at a dose of 5 mg/kg caused CFR's in all 5 animals in Group IV. The mean aortic pressure increased approximately 20 mmHg following L-NMMA infusion. After 30 minutes of consistent CFR's, extravascular intrapericardial sodium nitroprusside infusion at a dosage of 0.5 µg/kg/min abolished the CFR's within 10 to 30 minutes in all 5 dogs (p<0.01, FIGS. 8 and 9). The mean aortic pressure returned to the level before L-NMMA was infused. Oxyhemoglobin, infused into the proximal LAD coronary artery 30 minutes after CFR's were abolished with sodium nitroprusside, restored CFR's within 5 to 20 minutes in all 5 dogs (p<0.01, FIGS. 8 and 9). An average dose of 320±80 µg/kg/min of oxyhemoglobin was given to restore CFR's. The severity of the restored CFR's was similar to that of L-NMMA-induced CFR's in 3 of 5 animals and slightly less than that of the initial CFR's in the other 2 dogs. Mean aortic pressure was not significantly affected by oxyhemoglobin infusion.

These data indicate that nitric oxide does play an important role when extravascular intrapericardial sodium nitroprusside abolishes coronary CFR's.

Having now described in detail the methodology of our invention, those in the art will appreciate more than merely the detailed means described for implementing the invention, and our invention is not meant to be limited merely to these detailed implementations, but to all implementations comphrehended by our claims within the spirit of our invention.

We claim:

1. An apparatus comprising:
    an elongated catheter body having a proximal and distal segment,
    said body defining first and second lumens extending therethrough,
    first and second conductive leads within said body,
    said second lumen extending into a plurality of passages connecting said second lumen to the exterior of said distal segment,
    an expandable balloon mounted to an outer surface of said distal segment of said body to envelop said passages, thereby defining a balloon cavity between the balloon and said outer surface,
    a charge plate radially opposite said balloon and connected to said first lead,
    an iontophoretic pad radially opposite said balloon and adjacent to and in electroconductive contact with said charge plate,
    an electrode adjacent the periphery of said pad electrically insulated from said pad and charge plate, said electrode being connected to said second lead, and
    a catheter sheath surrounding at least a portion of said catheter body.

2. Apparatus comprising an elongate body having an expandable portion at a distal end with a charge plate on said distal end in electroconductive contact with an external iontophoretic pad on the charge plate, said pad containing a bioactive substance, said plate being connected to a first lead, with an electrode adjacent the periphery of said pad electrically insulated from said pad and charge plate and connected to a second lead, said first and second leads being contained in said body and exiting said body in a proximal segment thereof, said expandable portion of said distal end being connected by a lumen in the body that opens exteriorly at a proximal segment of the body for introduction thereinto of a pressurized fluid for expansion of said expandable portion.

3. Apparatus comprising:
    an elongated catheter body having a proximal and distal segment,
    said catheter body including a first lumen extending thereinto and exiting through at least one first passage in said distal segment,
    a second lumen in said catheter body extending to at least one second passage radially spaced from said first passage and connecting said second lumen to the exterior of said distal segment,
    a balloon mounted to at least a portion of the exterior of said distal segment enveloping said second passage while leaving said first passage unenveloped, providing a cavity between the balloon and the distal segment, said second passage opening into said cavity,
    an expandable bag mounted to an exterior surface of said distal segment, adjacent and radially opposite said balloon and over said first passage, thereby providing a chamber between the bag and said radially adjacent exterior surface into which said first passage opens, said bag comprising an iontophoretic pad,
    first and second electroconductive leads received in said body,
    a charge plate connected to said first lead and adjacent said pad in electroconductive contact therewith, and
    an electrode adjacent the periphery of said pad electrically insulated from said pad and charge plate and connected to said second lead.

4. The apparatus of claim 3 in which said iontophoretic pad contains a bioactive substance.

5. A method of delivering a bioactive substance, which comprises:
    percutaneously inserting into a patient and positioning outside an anatomical passageway and over a selected tissue surface a distal end of a distally expandable member having pores opening to the exterior of the distal end from a chamber provided upon expansion of said distal end, said chamber being connected by a lumen in the member that opens proximally exteriorly of the member, and
    introducing a gaseous fluid containing a bioactive substance into said lumen under pressure, thereby expanding said distal end of said member to press it against the tissue surface and deliver said bioactive substance through said pores at said tissue surface.

6. The method of claim 5 further comprising selecting the pericardium as said tissue surface.

7. The method of claim 6 further comprising selecting nitric oxide gas for said bioactive substance.

8. A method of delivering a bioactive substance, which comprises:
    providing an apparatus comprising an elongated catheter member having a proximal and distal segment, said catheter member including at least first and second lumens extending thereinto and exiting said catheter member through separate radially spaced first and second passages in said distal segment, a balloon mounted to at least a portion of the exterior of said catheter member distal segment and enveloping said second passage but not said first passage, thereby affording a balloon cavity between the balloon and said distal segment exterior, said second passage opening into said cavity, and an expandable bag mounted to an exterior surface of said distal segment of said catheter member adjacent and radially opposite said balloon and over said first passage, thereby affording a bag chamber between the bag and said radially adjacent exterior surface into which said first passage opens, said bag having pores for passage of fluid therethough to the exterior thereof radially opposite said balloon, percutaneously inserting said distal segment into a patient and positioning said distal segment outside an anatomical passageway and over a selected tissue surface, introducing a fluid through said second lumen to expand said balloon to press said bag of the distal segment against the tissue surface, and introducing a fluid containing a bioactive substance into said first lumen and delivering the fluid at said tissue surface from said pores of said bag.

9. The method of claim 8 in which said bag is predominantly laterally expandable.

10. The method of claim 8 further comprising selecting the pericardium as said tissue surface.

11. The method of claim 10 further comprising selecting a nitric oxide donor for said bioactive substance.

12. A method of delivering a bioactive substance, which comprises:

percutaneously inserting into a patient and positioning outside an anatomical passageway and over a selected tissue surface the distal end of a distally expandable member having an external iontophoretic pad containing a bioactive substance and in electroconductive contact with a radially inward charge plate connected to a first lead and with an electrode adjacent the periphery of said pad electrically insulated from said pad and charge plate and connected to a second lead, expanding said distally end of said member to press said iontophoretic pad against the tissue surface, and supplying voltage to said first lead to establish an electrical circuit with said second electrode and iontophoretically drive said bioactive substance from said pad into the tissue surface.

13. The method of claim 12 further comprising selecting the pericardium as said tissue surface.

14. The method of claim 13 further comprising selecting a nitric oxide donor for said bioactive substance.

15. A method of delivering a bioactive substance which comprises:

providing an apparatus comprising an elongated catheter member having a proximal and distal segment, said catheter member including at least first and second lumens extending thereinto and exiting said catheter member through separate radially spaced first and second passages in said distal segment, a balloon mounted to at least a portion of the exterior of said catheter member distal segment and enveloping said second passage but not said first passage, thereby affording a balloon cavity between the balloon and said distal segment exterior, said second passage opening into said cavity, an expandable bag mounted to an exterior surface of said distal segment of said catheter member adjacent and radially opposite said balloon and over said first passage, thereby providing a bag chamber between the bag and said radially adjacent exterior surface into which said first passage opens, said bag comprising an iontophoretic pad on an external surface, said apparatus further comprising first and second electroconductive leads in said member, a charge plate connected to said first lead and adjacent said pad in electroconductive contact therewith, and an electrode adjacent the periphery of said pad electrically insulated from said pad and charge plate and connected to said second lead, percutaneously inserting said distal segment into a patient and positioning said distal segment outside an anatomical passageway and over a selected tissue, introducing fluid through said first and second lumens to expand said balloon and bag to press said pad on the distal segment against the tissue surface, and supplying voltage to said first lead to establish an electrical circuit with said second electrode and iontophoretically drive said bioactive substance from said pad into the tissue surface.

16. The method of claim 15 in which said bag is predominantly laterally expandable.

17. The method of claim 15 in which said iontophoretic pad contains a bioactive substance.

18. The method of claim 15 further comprising selecting the pericardium as said tissue surface.

19. The method of claim 15 further comprising introducing a fluid containing a bioactive substance into said bag.

20. The method of claim 19 further comprising selecting a nitric oxide donor for said bioactive substance.

21. A method of delivering a bioactive substance, which comprises:

percutaneously inserting into a patient and positioning outside an anatomical passageway and over a selected tissue surface a distal end of a distally expandable member having pores opening to the exterior of the distal end from a chamber provided upon expansion of said distal end, said chamber being connected by a lumen in the member that opens proximally exteriorly of the member, introducing a fluid containing a bioactive substance into said lumen to expand said distal end, and causing said fluid to issue through said pores at the tissue surface.

22. The method of claim 21 further comprising selecting the pericardium as said tissue surface.

23. The method of claim 21 further comprising selecting a nitric oxide donor for said bioactive substance.

* * * * *